US012616981B2

(12) United States Patent
   Kusters

(10) Patent No.:  US 12,616,981 B2
(45) Date of Patent:       May 5, 2026

(54) SYSTEMS AND METHODS FOR FLUID SEPARATION INTERFACE CONTROL USING COLOR-BASED OPTICAL MEASUREMENTS

(71) Applicant: Fenwal, Inc., Lake Zurich, IL (US)

(72) Inventor: Benjamin E. Kusters, Pleasant Prairie, WI (US)

(73) Assignee: Fenwal, Inc., Lake Zurich, IL (US)

( * ) Notice: Subject to any disclaimer, the term of this patent is extended or adjusted under 35 U.S.C. 154(b) by 583 days.

(21) Appl. No.: 18/153,473

(22) Filed: Jan. 12, 2023

(65) Prior Publication Data

US 2023/0226562 A1      Jul. 20, 2023

Related U.S. Application Data

(60) Provisional application No. 63/299,654, filed on Jan. 14, 2022.

(51) Int. Cl.
   B04B 11/02        (2006.01)
   A61M 1/36        (2006.01)
   (Continued)

(52) U.S. Cl.
   CPC ........... B04B 11/02 (2013.01); A61M 1/3693 (2013.01); B04B 5/0442 (2013.01); G01N 13/00 (2013.01);
   (Continued)

(58) Field of Classification Search
   CPC . B04B 11/02; B04B 5/0442; B04B 2013/006; B04B 5/0428; A61M 1/3693;
   (Continued)

(56) References Cited

U.S. PATENT DOCUMENTS 5,194,145  A      3/1993   Schoendorfer
5,316,667  A      5/1994   Brown et al.
         (Continued)

FOREIGN PATENT DOCUMENTS

WO      WO 2018/053217 A1      3/2018

OTHER PUBLICATIONS

European Extended Search Report (EESR) from European Patent Application 23151261.7 dated Jun. 1, 2023; 7 pages.

*Primary Examiner* — Claire X Wang
*Assistant Examiner* — Shuyi S. Liu
(74) *Attorney, Agent, or Firm* — Cook Alex Ltd.

(57)      ABSTRACT

A fluid separation device includes a centrifugal separator configured to receive a centrifugal separation chamber of a disposable fluid flow circuit, a pump system configured to convey a fluid into the centrifugal separation chamber and to remove a separated fluid component from the centrifugal separation chamber via an outlet, a color-based interface monitoring system configured to determine an interface position between separated fluid components continuously flowing through the centrifugal separation chamber based on dominant wavelength measurements of layers of separated fluid components during a centrifugal separation procedure, and a controller configured to measure the dominant wavelengths of the layers, calculate a duration as a color time for each measured dominant wavelength, set target color times, calculate error signals and calculate control signals to adjust the pump system to control the flow rate and interface position.

17 Claims, 13 Drawing Sheets

10

(51) Int. Cl.
  B04B 5/04      (2006.01)
  G01N 13/00     (2006.01)
  B04B 13/00     (2006.01)
(52) U.S. Cl.
  CPC .... *A61M 2205/33* (2013.01); *B04B 2013/006*
                              (2013.01)
(58) Field of Classification Search
  CPC ............ A61M 2205/33; A61M 1/3609; A61M
            2205/3306; A61M 1/3696; A61M 1/029;
            G01N 13/00; G01N 33/49; G01N 15/05;
              G01N 33/491; G01N 21/6486; G01N
            2201/08; G01N 33/48; G01N 2015/012;
              G01N 2015/018; B01D 21/262; B01D
                                      2221/10
  USPC ............................................. 494/1, 3, 10, 84
  See application file for complete search history.

(56)                References Cited

U.S. PATENT DOCUMENTS

|  |  |  |  |  |
|---|---|---|---|---|
| 5,868,696 | A | 2/1999 | Giesler et al. | |
| 6,254,784 | B1 | 7/2001 | Nayak et al. | |
| 6,312,607 | B1 | 11/2001 | Brown et al. | |
| 10,919,235 | B2 | 2/2021 | Kusters et al. | |
| 11,465,160 | B2 | 10/2022 | Min et al. | |
| 2020/0166451 | A1* | 5/2020 | Kusters | G01N 21/251 |
| 2020/0368763 | A1 | 11/2020 | Kusters et al. | |

* cited by examiner

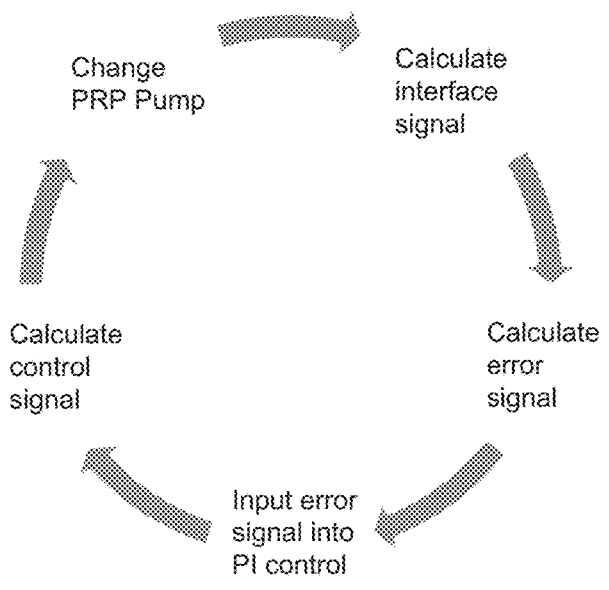
FIG. 3
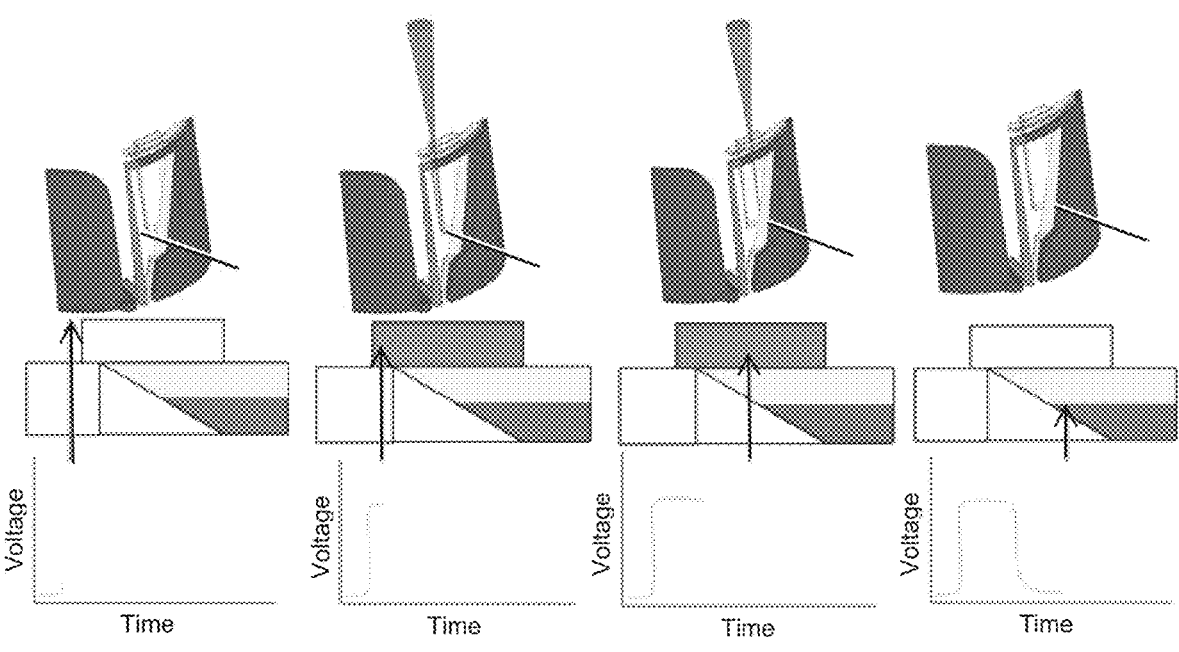
FIG. 4    (PRIOR ART)

130 — Measure wavelength

132 — Calculate duration for each wavelength:
Plasma Color Time
Buffy Color Time
RBC Color Time 134 — Set pre-determined Target Color Time
as setpoint
(Ex. Plasma Target Time)

136 — Calculate Error Signal
Plasma Target Time - Plasma Color Time

138 — Calculate PID terms and control signal

140 — Change Plasma flow rate

SYSTEMS AND METHODS FOR FLUID SEPARATION INTERFACE CONTROL USING COLOR-BASED OPTICAL MEASUREMENTS

CROSS-REFERENCE TO RELATED APPLICATIONS

This application claims the benefit of and priority to U.S. Provisional Patent Application Ser. No. 63/299,654, filed Jan. 14, 2022, the contents of which are incorporated by reference herein in their entirety.

BACKGROUND

Field of the Disclosure

The present disclosure relates to centrifugal separation of a biological fluid. More particularly, the present disclosure relates to improved systems and methods for control of an interface position between separated fluid components during fluid separation procedures.

Description of Related Art

Various blood processing systems now make it possible to collect particular blood constituents, rather than whole blood from a blood source, such as a human donor or patient. Typically, in such systems, whole blood is drawn from a source, the particular blood component or constituent is separated, removed and collected, and the remaining blood constituents are returned to the source. Removing only particular constituents is advantageous when the blood source is a donor, because potentially less time is needed for the donor's body to return to normal or pre-donation levels. Also, donations of particular blood components or constituents may be made at more frequent intervals than when whole blood is collected. This increases the overall supply of blood constituents, such as plasma and platelets, made available for transfer and/or therapeutic treatment or health care.

Whole blood is typically separated into its constituents through centrifugation. This requires that the whole blood be passed through a centrifuge assembly or centrifugal separator after it is withdrawn from, and before it is returned to, the blood source. To avoid contamination and possible infection of the source, the blood is preferably contained and processed within a disposable, sealed, sterile fluid flow circuit or fluid processing assembly during the entire centrifugation process. Typical blood processing systems thus include a permanent or reusable centrifuge assembly containing hardware (centrifuge, drive system, pumps, valve actuators, programmable controller, and the like) that rotates a centrifugal separator and controls the flow through the disposable, sealed and sterile fluid flow circuit that is mounted on and in cooperation with the hardware. The centrifuge assembly engages and rotates a centrifugal separation chamber of the disposable fluid processing assembly during a collection procedure. The blood, however, makes actual contact only with the fluid processing assembly, which assembly is used only once and then discarded.

Prior to or shortly after loading a disposable fluid flow circuit into the centrifuge assembly, the operator typically enters, for example, by means of a touch screen or other user interface system, a particular processing protocol to be executed by the system (e.g., a procedure wherein platelets are separated from whole blood and collected) and other parameters (e.g., the weight of the donor, the desired volume of the separated blood component to be collected, etc.). When the system has been programmed, the operator phlebotomizes a donor and the system carries out the procedure, under the supervision of the operator.

As the centrifuge assembly rotates the centrifugal separation chamber of the disposable fluid flow circuit, the heavier (greater specific gravity) components of the whole blood in the separation chamber, such as red blood cells, move radially outwardly away from the center of rotation toward the outer or "high-G" wall of the separation chamber. The lighter (lower specific gravity) components, such as plasma, migrate toward the inner or "low-G" wall of the separation chamber. Various components can be selectively removed from the whole blood by including appropriately located channeling structures and outlet ports in the separation chamber of the disposable fluid flow circuit. For example, therapeutic plasma exchange involves separating plasma from cellular blood components, collecting the plasma, and returning the cellular blood components and a replacement fluid to the blood source. Alternatively, red blood cells may be harvested from the separation chamber and the rest of the blood constituents returned to the donor. Other processes are also possible including, without limitation, platelet collection, red blood cell exchanges, plasma exchanges, etc.

Proper separation requires, however, that the interface between the separated components be located within a particular zone between the high-G and low-G walls of the separation chamber. For example, when performing a therapeutic plasma exchange procedure, the interface between the plasma and the cellular blood components affects the performance of the system. If the interface is located too close to the low-G wall, then the collected plasma may become unduly populated or contaminated by cellular blood components. On the other hand, if the interface is located too far from the low-G wall, there may be no contamination of the plasma, but the separation efficiency may be decreased with less plasma collected over time.

Various centrifuges, such as those shown and described in U.S. Pat. No. 6,254,784 to Nayak et al., U.S. Pat. No. 6,312,607 to Brown et al. and U.S. Pat. No. 11,465,160 to Min et al. (which are incorporated herein by reference), are operable to automatically keep the interface within a desired zone as the centrifuge operates. Typically, the separation chamber of the fluid processing assembly is loaded between the bowl and spool of a centrifuge. A radially inwardly ramped surface is located on the radially outer wall of the separation channel in the bowl wall of the separation chamber. The interface between the generally dark, opaque red blood cell layer and the generally light, clear plasma layer appears as a line on the ramped surface of the interface ramp. Where, exactly, the line appears on the ramped surface is a function of the position of the interface between the high-G and low-G walls of the separation chamber. Accordingly, the position of the line on the ramped surface can be used to gauge the position of the interface between the high-G and low-G walls.

Automatic control over the position of the interface has been achieved by sensing the position of the line on the ramped surface and thereafter adjusting the centrifuge operating parameters to place and keep the line within desired limits. In particular, by controlling the rate at which plasma is withdrawn from the separation chamber, the line can be "moved" up (radially inwardly) or down (radially outwardly) on the ramped surface, such as by decreasing or increasing the plasma flow rate.

An optical sensor assembly may be used to sense the position of the line on the ramped surface. Optical control systems commonly operate based on the principle that light will transmit through optically clear fluid, such as saline and plasma (platelet rich plasma, PRP, or plasma poor plasma, PPP), while light will not transmit through optically dense fluid, such as whole blood, WB, or packed Red Blood Cells, RBCs. Thus, when using a light source and detector apparatus, as in the prior systems, optical signals representative of the optical clear fluid thickness within a centrifuge can be measured and applied to calculate and maintain the position of the RBC/plasma interface or interface position.

As the centrifuge rotates past the sensor, the sensor develops an electrical pulse having a width related to the position of the line on the ramped surface. As the line moves closer to the high-G wall of the separation chamber, the pulse width increases. As the line moves closer to the low-G wall, the pulse width narrows. By sensing the width of the pulses developed by the optical sensor and thereafter using the pulse width to increase or decrease the rate at which plasma is withdrawn from the separation chamber, the system attempts to keep the line within desired positional limits on the ramped surface and to maintain the interface in the desired radial position or range of positions.

At the start of a separation procedure, saline may be present in the centrifuge during a calibration phase and a light source, such as a laser light, will be transmitted through the entire width of the centrifuge ramp. The signal produced is referred to as the Saline Calibration Signal and represents the width of the entire centrifuge gap without any RBCs present. This signal serves as the reference for calculating the RBC/plasma interface position throughout a procedure. The RBC/plasma interface position is defined as the percentage of the Saline Calibration Signal covered by RBCs. For example, an interface position of 40% signifies that 40% of the original Saline Calibration Signal is blocked by RBCs.

The interface position is indicative of the RBC bed thickness in the centrifuge but is not a literal representation of the RBC bed. That is, an interface position of 40% does necessarily correlate to an RBC bed that takes up 40% of the centrifuge gap between the high-G and low-G walls. FIG. 1 displays an example of signals produced by a photodetector for the saline calibration and increasing RBC bed thickness. The pulse width, PW, of the voltage signal, represented as the measurement threshold by dual sided arrows in FIG. 1, is measured in time and is the key signal characteristic applied in the calculation of the interface position. The PW is a measurement taken at a predetermined voltage threshold, such as 20% of the signal amplitude. FIG. 1 represents cross sections of the fluid gap and the optical signal PW is shown for the saline S calibration (at left, e.g., PW=800 μs) relative to increasing RBC bed thickness, which is represented by the PW for the plasma, such as PRP or PPP, decreasing from (at center, e.g., PW=600 μs to at right PW=400 μs) as RBCs build up in the fluid gap, in turn, decreasing the plasma width through which light can be transmitted.

Thus, the system controller may compare the PW of a measured signal during processing to the PW generated during the saline calibration phase, which corresponds to the pulse width when light is transmitted to the light detector over the entire width of the ramp. Comparing these two PWs will indicate the percentage of the ramp that is occupied by the plasma layer and by the RBC layer, which information the controller may use to determine the position of the interface position INT within the channel. In particular, the interface position may be calculated as follows:

$$\text{Interface Position (\%)} = [(\text{Saline Calibration Pulse Width} - \text{Current Plasma Pulse Width})/\text{Saline Calibration Pulse Width}] \times 100.$$

Once the interface position is calculated, it is compared to an ideal, target or targeted position, known as the interface position Setpoint. The difference between the calculated interface position INT and the interface position Setpoint is considered the Error Signal (Error Signal=Setpoint–Interface Position), which represents how far the interface position INT is from where it should ideally be located, as depicted in FIG. 2.

The Error Signal is fed into a proportional integral, PI, or proportional-integral-derivative, PID, based control loop in a controller to calculate the plasma rate required to bring the Interface Position INT closer to the Setpoint, based on how far the Interface Position INT is from the Setpoint (Proportional Term, P), and how long and how far the Interface Position INT has been from Setpoint (Integral Term, I) for a PI controller, and also including the rate of change of the Interface Position (Derivative Term, D) for a PID controller. An example controller control loop is represented in FIG. 3. In general, a slower PRP rate will lower the Interface Position toward the high-G wall, while a faster PRP rate will raise the Interface Position toward the low-G wall.

Thus, it is known to employ an optical sensor system to monitor the flow of blood and/or blood components through the fluid flow circuit in the centrifuge and determine various characteristics of the flow. For example, U.S. Pat. No. 6,899,666 (which is hereby incorporated herein by reference) relates to an optical sensor system for viewing into the centrifugal separation chamber for detecting and controlling the position of an interface between separated blood components in a centrifuge. Indeed, all prior art using an optical sensor known to the inventor applies simple light transmission measurements for control of an interface and fluid layers within a centrifuge. In such systems, the light also must be further transmitted to a detector to be measured, such as by a prism, as shown in FIG. 4 and described in the above-referenced patent application. While such systems function satisfactorily, one limitation of such systems is the requirement for light to transmit through the plasma layer, which may become problematic when the plasma layer becomes less optically clear, such is the case with lipemic plasma.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

This disclosure provides unique systems and methods that utilize color measurements for control of the fluid layers within a continuous flow fluid separation centrifuge. Known prior art systems use simple light transmission measurements through fluid at a fluid separation interface for control of fluid layers in a centrifuge, without determining and using the dominant wavelength of color for each layer. The systems and methods of the present disclosure measure the main dominant wavelength of the colors of the respective fluid layers (such as, yellow, white and red) over time to determine fluid layer thicknesses. In general, the longer the time a particular dominant wavelength is measured as present, the thicker the fluid layer will be, and vice versa. The measured duration of a fluid's color, otherwise referred to herein as the color time, can be compared to a target duration or target color time, and used to control flow rates into and out of a centrifuge to obtain desired fluid thicknesses, thereby adjusting the interface position. A major advantage over current transmission-based systems is that the optical clarity of the plasma layer will no longer impact the interface control system, as long as the plasma remains tinted yellow. This will allow the control system to successfully complete procedures containing lipemic plasma that are currently problematic for transmission measurement methods.

Thus, the present disclosure eliminates the requirement to measure light transmission through a fluid, such as a plasma layer, by instead measuring the color of the fluid layers via reflectance spectroscopy or by any other suitable alternative color measurement technique. This will enable a color-based interface control system that relies only on the color of the fluid layers, without concern for optical clarity of the fluid layers. Furthermore, the color-based method may differentiate a between layers that may be similar with respect to opacity by instead relying on color measurement of the respective fluid layers. This is particularly advantageous when distinguishing because cells of different layers that prevent the transmission of light, such as may occur for example with more opaque layers including a white buffy coat layer and a red RBC layer.

In one aspect, a fluid separation device is provided and includes a centrifugal separator configured to receive a centrifugal separation chamber of a disposable fluid flow circuit, a pump system configured to convey a fluid into the centrifugal separation chamber, and to remove a separated fluid component from the centrifugal separation chamber, an outlet associated with the centrifugal separation chamber for removing at least a portion of the separated fluid component from the centrifugal separation chamber, a color-based interface monitoring system configured to determine an interface position between separated fluid components continuously flowing through the centrifugal separation chamber based on color measurements of layers of the fluid during a centrifugal separation procedure, and a controller. The controller is configured to control the pump system to convey a fluid into the centrifugal separation chamber, control the centrifugal separator to separate the fluid in the centrifugal separation chamber into layers of separated fluid components with the interface located between the layers of separated fluid components, measure a color of each layer of the respective separated fluid components via a dominant wavelength of reflected light, calculate a duration for each dominant wavelength associated with the respective layers of separated fluid components, set a predetermined target color time as a setpoint for each layer, calculate an error signal, and utilize the error signal and calculate proportional-integral-derivative terms and a control signal that changes a pump system setting so as to adjust the interface position.

In another aspect, the disclosure provides a method of adjusting a target position of an interface between separated fluid components continuously flowing through a centrifuge that includes separating fluid in a centrifuge into layers of separated fluid components with an interface between the separated layers, measuring a color dominant wavelength of each layer, calculating a duration as a color time for each measured dominant wavelength relative to each layer, setting a predetermined target color time as a set point for a selected layer, calculating an error signal equal to the target color time minus the calculated color time for the selected layer, calculating proportional-integral-derivative terms and a control signal, and using the control signal to change a flow rate of the separated fluid components through the centrifuge to adjust the interface position.

In yet another aspect, a blood separation system is provided and includes a centrifugal separator configured to receive a centrifugal blood separation chamber of a disposable fluid flow circuit and to process blood to separate at least one cellular component from plasma, a pump system configured to move the plasma in the disposable fluid flow circuit, an outlet associated with the blood separation chamber for removing at least a portion of the plasma from the blood separation chamber, a color-based interface monitoring system configured to directly monitor the interior of the blood separation chamber and to determine an interface position between the separated component and the plasma during a centrifugal separation procedure, and a controller. The controller is configured to control the pump system to convey a fluid into the centrifugal separation chamber, control the centrifugal separator to separate the blood in the centrifugal separation chamber into layers of plasma and the separated at least one cellular component with the interface located between the layers, measure a color of each layer via a dominant wavelength of reflected light, calculate a duration for each measured dominant wavelength associated with the respective layers, set a predetermined target color time as a setpoint for a selected layer, calculate an error signal, and utilize the error signal and calculate proportional-integral-derivative terms and a control signal that changes a pump system setting so as to adjust the interface position.

BRIEF DESCRIPTION OF DRAWINGS

FIG. 3 is a diagram of an control loop of a system controller that seeks to calculate a control signal to change the PRP pump, to then calculate the interface signal in an effort to set the Setpoint to a higher value, which is followed by calculation of an Error Signal and then inputting the Error Signal into the controller to continue to revise the processing toward a higher ideal interface position;

FIG. 4 is a schematic diagram of a prior art method that requires light transmission through a fluid to a light detector and progression of a signal as the fluid becomes less optically clear;

DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

FIGS. 1-22 provide background information and show components of a blood or fluid separation system that embodies various aspects of the present subject matter. While the system may be described herein in terms of its use in separating blood into two or more components, it should be understood that systems according to the present disclosure can be used for processing a variety of biological or bodily fluids, including fluids containing both bodily and non-bodily fluids (e.g., anticoagulated blood).

Figure 1:
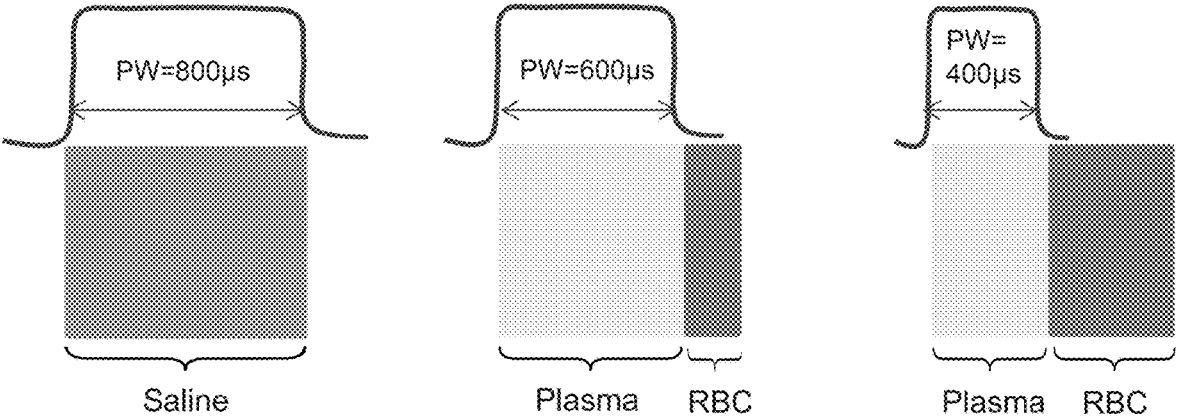
FIG. 1 is a series of schematic diagrams of example optical signal pulse width measurements at cross sections of a fluid gap representing saline, and decreasing pulse width as RBC builds up in the fluid gap thus decreasing the plasma width through which light can be transmitted.
Figure 2:
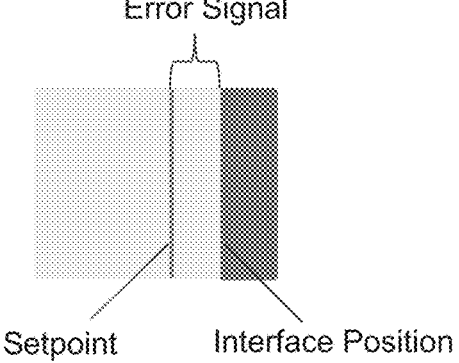
FIG. 2 is a schematic diagram of an example error signal shown as being equal to the Setpoint-Interface Position.
Figure 5:
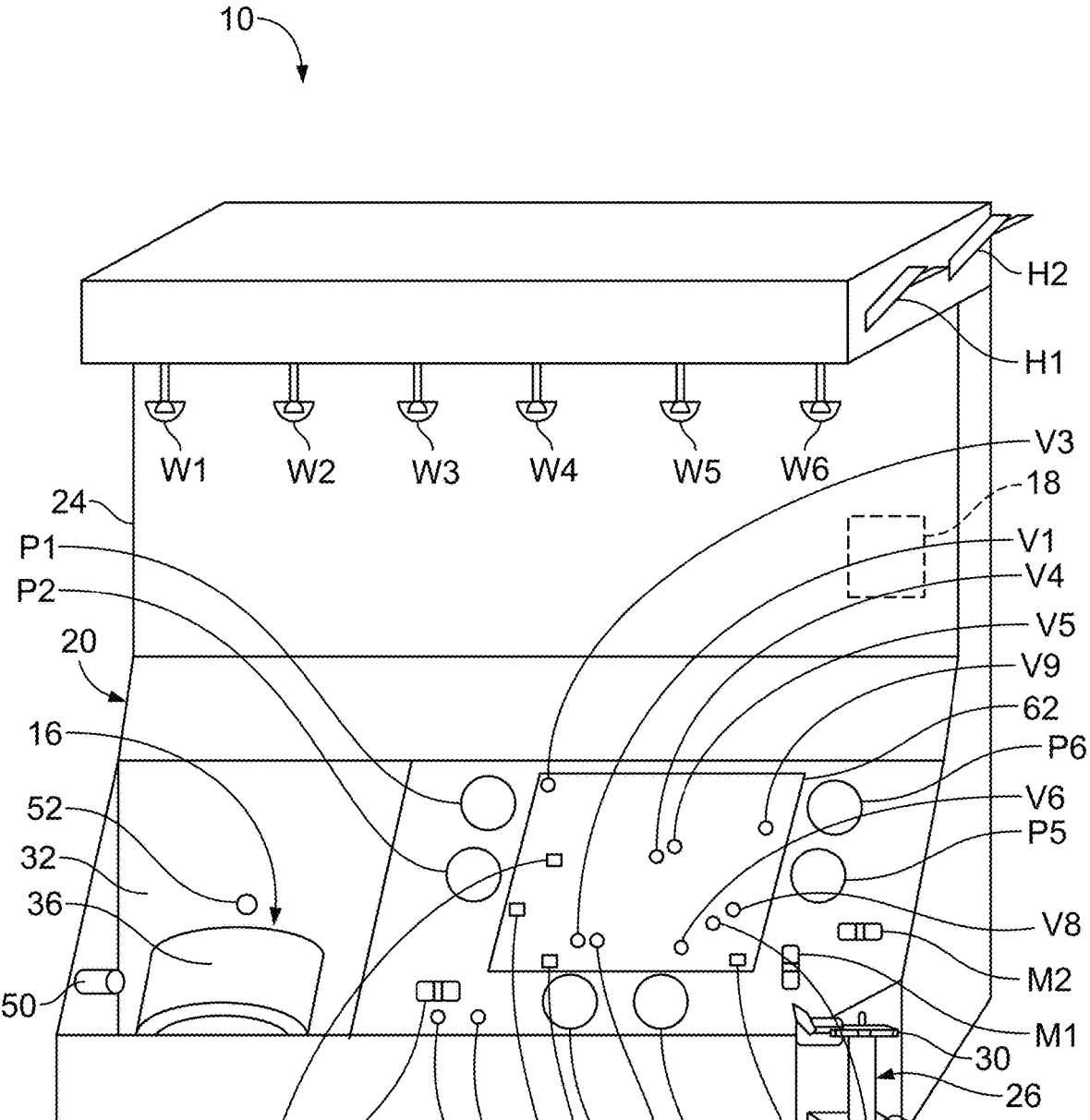
FIG. 5 is a perspective view of an exemplary fluid separation device that comprises a component of a fluid separation system according to an aspect of the present disclosure.
Figure 6:
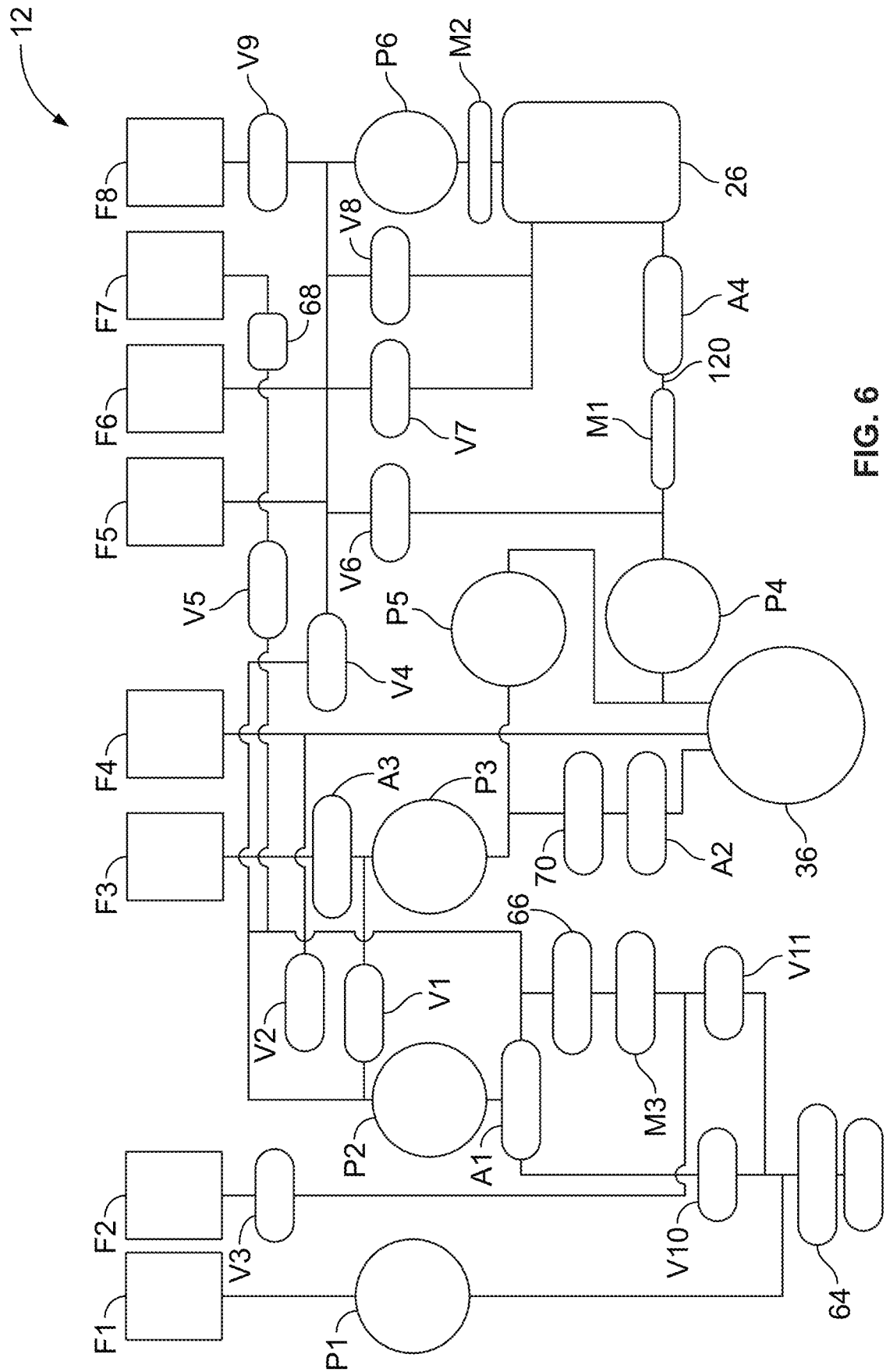
FIG. 6 is a schematic view of an exemplary disposable fluid flow circuit that may be mounted to the fluid separation device of FIG. 5 to complete a fluid separation system according to an aspect of the present disclosure.

Generally speaking, the system includes two principal components, a durable and reusable fluid separation device 10 (FIG. 5) and a disposable fluid flow circuit 12 (FIG. 6). The fluid separation device 10 of this example includes a spinning membrane separator drive unit 14 (FIG. 5), a centrifuge or centrifugal separator 16 (FIG. 7), additional components that control fluid flow through the disposable fluid flow circuit 12, and a controller 18 (FIG. 5), which governs the operation of the components of the fluid separation device 10 to perform a fluid processing and collection procedure selected by the operator. Much of the two principal components of the present disclosure are similar to those disclosed in U.S. Pat. No. 10,919,235 (which is hereby incorporated herein by reference). The interface adjustment principles described herein are not limited to any particular fluid separation procedures, so no complete fluid separation procedure will be described in detail herein. However, reference may be made to PCT Patent Application Publication No. WO 2018/053217 A1 (which is hereby incorporated herein by reference) for descriptions of various exemplary fluid separation procedures that may be carried out using the system described herein and which may be practiced in combination with the interface adjustment principles described herein.

I. The Durable Fluid Separation Device

The fluid separation device 10 (FIG. 5) is configured as a durable item that is capable of long-term use. It should be understood that the fluid separation device 10 of FIG. 5 is merely exemplary of one possible configuration and that fluid separation devices according to the present disclosure may be differently configured. For example, it is within the scope of the present disclosure for the fluid separation device to omit a spinning membrane separator drive unit 14 and to include only a centrifugal separator 16.

In the illustrated embodiment, the fluid separation device 10 is embodied in a single housing or case 20. The illustrated case 20 includes a generally horizontal portion 22 (which may include an inclined or angled face or upper surface for enhanced visibility and ergonomics) and a generally vertical portion 24. The spinning membrane separator drive unit 14 and the centrifugal separator 16 are shown as being incorporated into the generally horizontal portion 22 of the case 20, while the controller 18 is shown as being incorporated into the generally vertical portion 24. The configuration and operation of the centrifugal separator 16, the controller 18, and selected other components of the fluid separation device 10 will be described in greater detail.

In the illustrated embodiment, the generally horizontal portion 22 is intended to rest on an elevated, generally horizontal support surface (e.g., a countertop or a tabletop), but it also is within the scope of the present disclosure for the case 20 to include a support base to allow the case 20 to be appropriately positioned and oriented when placed onto a floor or ground surface. It also is within the scope of the present disclosure for the case 20 to be mounted to a generally vertical surface (e.g., a wall), by either fixedly or removably securing the generally vertical portion 24 of the case 20 to the generally vertical surface.

The case 20 may be configured to assume only the position or configuration of FIG. 5 or may be configured to move between two or more positions or configurations. For example, in one embodiment, the generally horizontal and vertical portions 22 and 24 may be joined by a hinge or pivot, which allows the case 20 to be moved between a functional or open configuration (FIG. 5) in which the generally vertical portion 24 is oriented at approximately 90 degrees to the generally horizontal portion 22, and a transport or closed configuration in which the generally vertical portion 24 is rotated about the hinge toward the generally horizontal portion 22. In such a reconfigurable embodiment, the generally vertical portion 24 may be considered to be the lid of the case 20, while the generally horizontal portion 22 may be considered to be the base. If the case 20 is reconfigurable, then it may include a latch for releasably locking the case 20 in its transport or closed configuration and/or a handle, which the operator may grasp for transporting the case 20 in its closed configuration.

While it may be advantageous for the fluid separation device 10 to be embodied in a compact, portable case 20, it also is within the scope of the present disclosure for the fluid separation device to be embodied in a larger case or fixture that is intended to be installed in a single location and remain in that location for an extended period of time. If the fluid separation device is provided as such a fixture, it may be provided with more components and functionality than a more portable version.

Spinning Membrane Separator Drive Unit

The illustrated fluid separation device 10 includes a spinner support or spinning membrane separator drive unit 14 (FIG. 5) for accommodating a generally cylindrical spinning membrane separator 26 of a fluid flow circuit 12 (FIG. 6). U.S. Pat. No. 5,194,145 (which is hereby incorporated herein by reference) describes an exemplary spinning membrane separator drive unit that would be suitable for incorporation into the fluid separation device 10. However, it should be understood that the spinning membrane separator drive unit 14 may be differently configured without departing from the scope of the present disclosure. The interface determination principles described herein also may be practiced in the absence of a spinning membrane separator, so the spinning membrane separator drive unit 14 is not described in detail herein.

Centrifugal Separator

Figure 7:
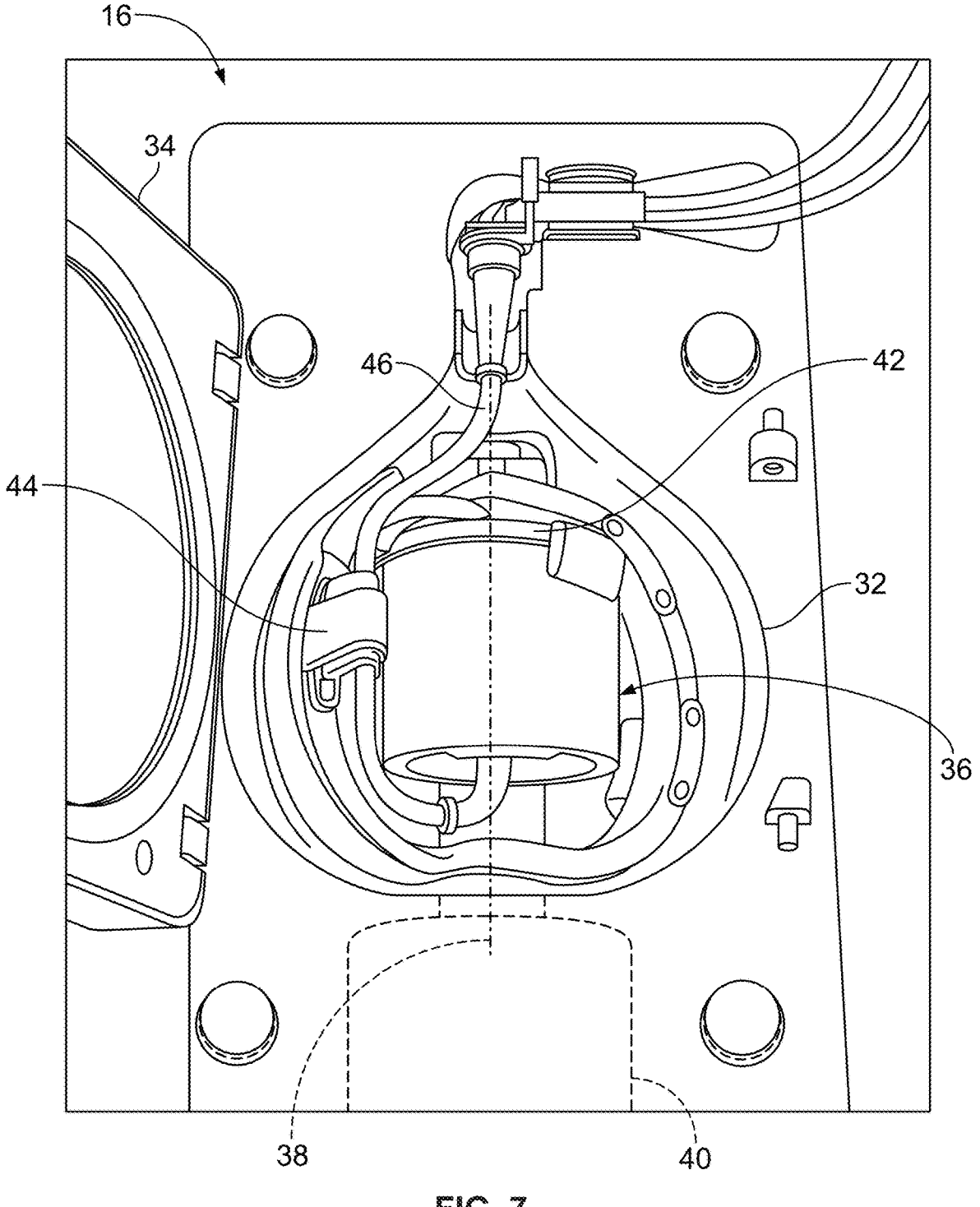
FIG. 7 is a perspective view of an exemplary centrifugal separator of the fluid separation device of FIG. 5, with the centrifugal separation chamber of a fluid flow circuit mounted therein.

As for the centrifuge or centrifugal separator 16, it includes a centrifuge compartment 32 that may receive other components of the centrifugal separator 16 (FIG. 7). The centrifuge compartment 32 may include a lid 34 that is opened to insert and remove a centrifugal separation chamber 36 of the fluid flow circuit 12. During a separation procedure, the lid 34 may be closed with the centrifugal separation chamber 36 positioned within the centrifuge compartment 32, as the centrifugal separation chamber 36 is spun or rotated about an axis 38 under the power of an electric drive motor or rotor 40 of the centrifugal separator 16.

The particular configuration and operation of the centrifugal separator 16 depends upon the particular configuration of the centrifugal separation chamber 36 of the fluid flow circuit 12. In one embodiment, the centrifugal separator 16 is similar in structure and operation to that of the ALYX system manufactured by Fenwal, Inc. of Lake Zurich, Illinois, which is an affiliate of Fresenius Kabi AG of Bad Homburg, Germany, as described in greater detail in U.S. Pat. No. 8,075,468, which is hereby incorporated herein by reference.

Figure 8:
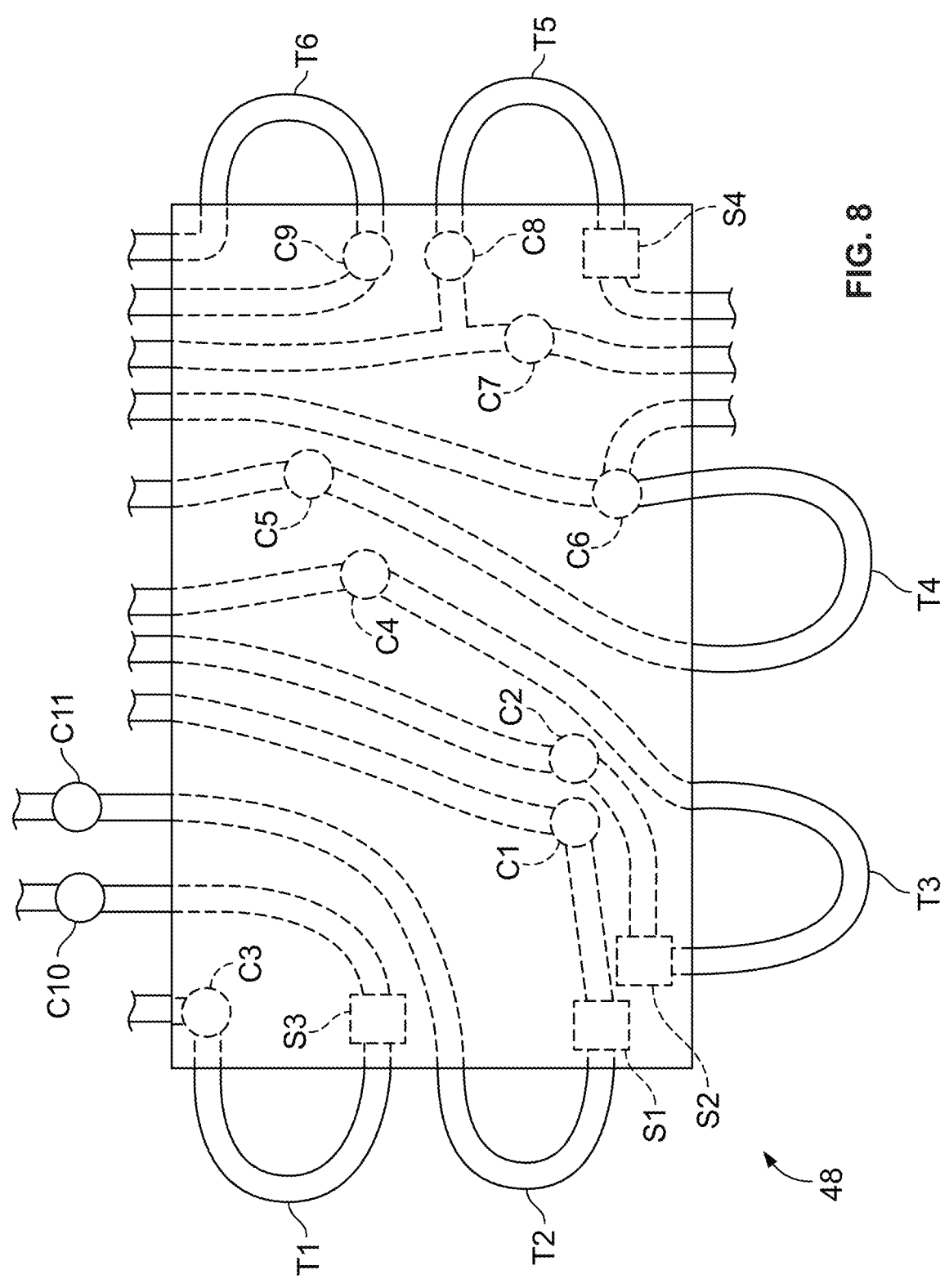
FIG. 8 is a top plan view of an exemplary cassette of a fluid flow circuit, which can be actuated to perform a variety of different fluid processing procedures in association with the fluid separation device of FIG. 5.

More particularly, the centrifugal separator 16 may include a carriage or support 42 that holds the centrifugal separation chamber 36 and a yoke member 44. The yoke member 44 engages an umbilicus 46 of the fluid flow circuit 12, which extends between the centrifugal separation chamber 36 and a cassette 48 of the fluid flow circuit 12 (FIG. 8). The yoke member 44 causes the umbilicus 46 to orbit around the centrifugal separation chamber 36 at a one omega rotational speed. The umbilicus 46 twists about its own axis as it orbits around the centrifugal separation chamber 36. The twisting of the umbilicus 46 about its axis as it rotates at one omega with the yoke member 44 imparts a two omega rotation to the centrifugal separation chamber 36, according to known design. The relative rotation of the yoke member 44 at a one omega rotational speed and the centrifugal separation chamber 36 at a two omega rotational speed keeps the umbilicus 46 untwisted, avoiding the need for rotating seals.

A fluid is introduced into the centrifugal separation chamber 36 through the umbilicus 46, with the fluid being separated (e.g., into a layer of less dense components, such as platelet-rich plasma, if the fluid is blood, and a layer of more dense components, such as packed red blood cells, if the fluid is blood) within the centrifugal separation chamber 36 as a result of centrifugal forces as it rotates. Components of an interface monitoring system may be positioned within the centrifuge compartment 32 to oversee separation of blood within the centrifugal separation chamber 36. As shown with respect to FIGS. 9-13 and described in greater detail herein, a color-based interface monitoring system 50 may include a light source 52 and a spectrometer 54, which are connected to an optical fiber bundle 56. The optical fiber bundle 54 is positioned and oriented at an acute angle Θ relative to the surface of the centrifugal separation chamber 36 to carry light from light source 52 to the fluid F in the centrifugal separation chamber 36 via at least one optical fiber 58, and to carry light reflected directly back toward the light source to the spectrometer 54 via at least one optical fiber 60.

Figure 12:
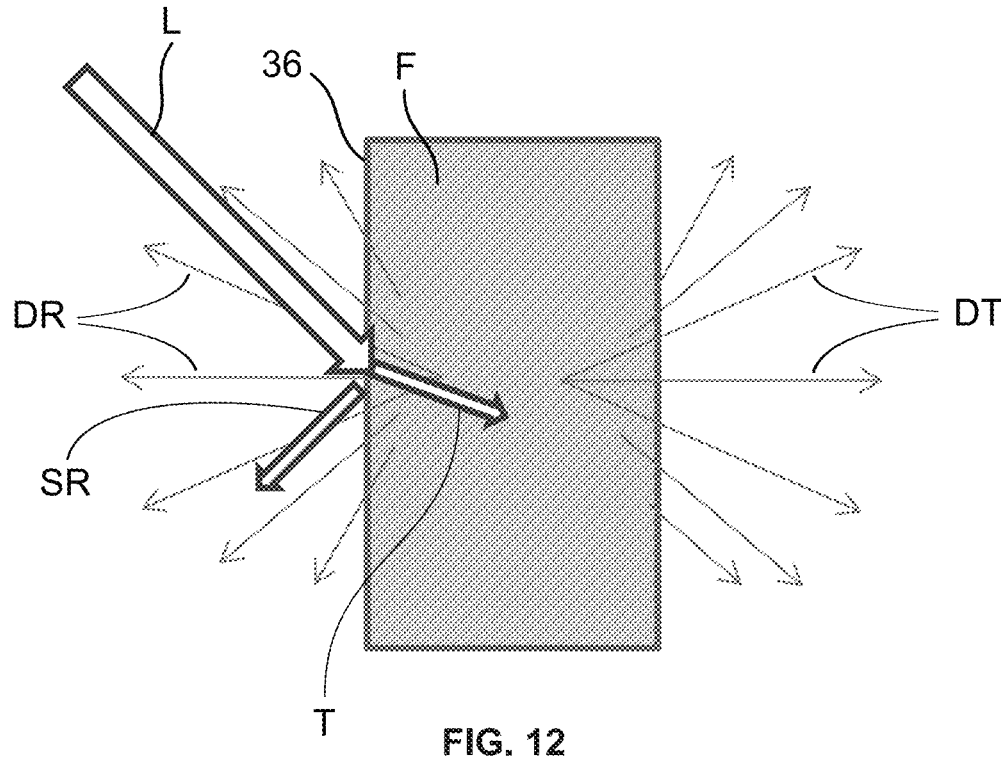
FIG. 12 is a simplified diagram indicating the distribution of light from the incident light source of the color-based interface monitoring system.
Figure 13:
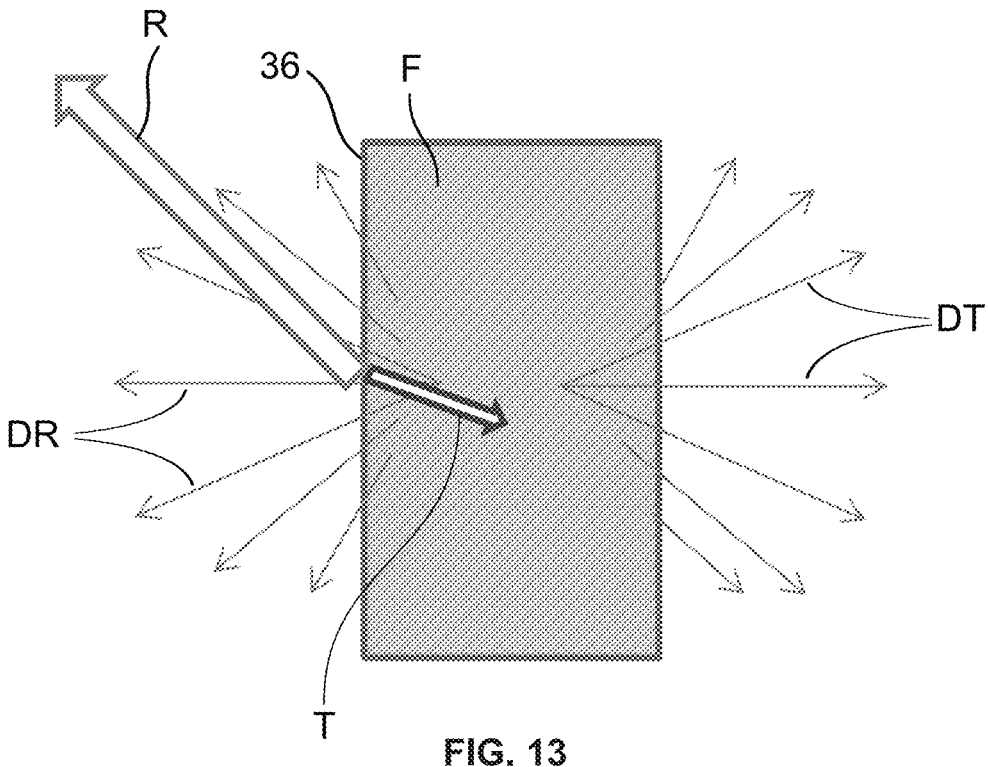
FIG. 13 is a simplified diagram indicating the reflective light carried to the spectrometer of the color-based interface monitoring system.

FIGS. 12 and 13 demonstrate the reflective and transmissive properties of light from the light source 52. In FIG. 12, when light L is carried from the light source 52 to the surface of the centrifugal separation chamber 36, specular reflection will have some of the incident light SR reflected off the surface and away at an equivalent acute angle Θ. Some of the light will be transmitted across the surface and into the fluid as transmitted light T at an angle according to Snell's Law, with some of the transmitted light T absorbed by the fluid and some subject to diffuse reflectance DR while other is subject to diffuse transmission DT. As shown in FIG. 13, some of the light L from the light source will be reflected light R, which is reflected directly back toward the incident light L and is carried by an optical fiber 60 to the spectrometer 54.

Preferably, the light source 52 and the spectrometer are positioned in the case 20 and the optical bundle 56 is connected to a stationary surface of the centrifuge compartment 32.

The orientation of the various components of the color-based interface monitoring system 50 depends at least in part on the particular configuration of the centrifugal separation chamber 36, which will be described in greater detail herein. In general, though, the light source 52 emits a broadband light source (such as may be provided by Thorlabs Stabilized Tungsten-Halogen Light Source, PN SLS201 L, 360-2600 nm, or equivalent). At a minimum, the light source will include all wavelengths in the visible range (e.g., approximately 400-700 nm), but may contain wavelengths above or below this range.

The light L is carried by at least on optical fiber 58 in the optical bundle 56 and is directed at the separated fluid components within the centrifugal separation chamber 36 (which may be formed of a material that substantially transmits the light or at least a particular wavelength range of the light without absorbing it). The optical bundle 56 is directed at the acute angle Θ relative to the surface of the centrifugal separation chamber 36 and a portion of the light is reflected back the optical bundle 56 and is carried by at least one optical fiber 60 to the spectrometer 54. If the controller 18 determines that the interface is in the wrong position (which can affect the separation efficiency of the centrifugal separator 16 and/or the quality of the separated blood components), then it can issue commands to the appropriate components of the fluid separation device 10 to modify their operation, so as to move the interface to the proper position.

Other Components of the Fluid Separation Device

In addition to the spinning membrane separator drive unit 14 and the centrifugal separator 16, the fluid separation device 10 may include other components compactly arranged to aid fluid processing.

The generally horizontal portion 22 of the case 20 of the illustrated fluid separation device 10 includes a cassette station 62 (FIG. 5), which accommodates a cassette 48 (FIG. 8) of the fluid flow circuit 12. In one embodiment, the cassette station 62 is similarly configured to the cassette station of U.S. Pat. No. 5,868,696 (which is hereby incorporated herein by reference), and shown corresponding more closely to the apparatus in U.S. Pat. No. 10,919,235 (previously incorporated herein by reference), but is adapted to include additional components and functionality. The illustrated cassette station 62 includes a plurality of clamps or valves V1-V9 (FIG. 5), which move between a plurality of positions (e.g., between a retracted or lowered position and an actuated or raised position) to selectively contact or otherwise interact with corresponding valve stations C1-C9 of the cassette 48 of the fluid flow circuit 12 (FIGS. 6 and 8). Depending on the configuration of the fluid flow circuit 12, its cassette 48 may not include a valve station C1-C9 for each respective valve V1-V9 of the cassette station 62, in which case fewer than all of the valves V1-V9 will be used in a separation procedure.

In the actuated position, a valve V1-V9 engages the associated valve station C1-C9 to prevent fluid flow through that valve station C1-C9 (e.g., by closing one or more ports associated with the valve station C1-C9, thereby preventing fluid flow through that port or ports). In the retracted position, a valve V1-V9 is disengaged from the associated valve station C1-C9 (or less forcefully contacts the associated valve station C1-C9 than when in the actuated position) to allow fluid flow through that valve station C1-C9 (e.g., by opening one or more ports associated with the valve station C1-C9, thereby allowing fluid flow through that port or ports). Additional clamps or valves V10 and V11 may be positioned outside of the cassette station 62 to interact with portions or valve stations C10 and C11 (which may be lengths of tubing) of the fluid flow circuit 12 to selectively allow and prevent fluid flow therethrough. The valves V1-V9 and corresponding valve stations C1-C9 of the cassette station 62 and cassette 48 may be differently configured and operate differently from the valves V10 and V11 and valve stations C10 and C11 that are spaced away from the cassette station 62.

The cassette station 62 may be provided with additional components, such as pressure sensors A1-A4, which interact with sensor stations S1-S4 of the cassette 48 to monitor the pressure at various locations of the fluid flow circuit 12. For example, if the fluid source is a human donor, one or more of the pressure sensors A1-A4 may be configured to monitor the pressure of the donor's vein during blood draw and return. Other pressure sensors A1-A4 may monitor the pressure of the spinning membrane separator 26 and the centrifugal separation chamber 36. The controller 18 may receive signals from the pressure sensor A1-A4 that are indicative of the pressure within the fluid flow circuit 12 and, if a signal indicates a low or high-pressure condition, the controller 18 may initiate an alarm or error condition to alert an operator to the condition and/or to attempt to bring the pressure to an acceptable level without operator intervention.

The fluid separation device 10 may also include a pump system having a plurality of pumps P1-P6 to cause fluid to flow through the fluid flow circuit 12. The pumps P1-P6 may be differently or similarly configured and/or function similarly or differently from each other. In the illustrated embodiment, the pumps P1-P6 are configured as peristaltic pumps, which may be generally configured as described in U.S. Pat. No. 5,868,696. Each pump P1-P6 engages a different tubing loop T1-T6 extending from a side surface of the cassette 48 (FIG. 8) and may be selectively operated under command of the controller 18 to cause fluid to flow through a portion of the fluid flow circuit 12. In one embodiment, all or a portion of the cassette station 62 may be capable of translational motion into and out of the case 20 to allow for automatic loading of the tubing loops T1-T6 into the associated pump P1-P6.

The illustrated fluid separation device 10 optionally includes a centrifuge outlet sensor M1 for determining one or more properties of fluids flowing out of the centrifugal separator 16. If the fluid flowing out of the centrifugal separator 16 includes red blood cells, the centrifuge outlet sensor M1 may be configured to determine the hematocrit of the fluid. If the fluid flowing out of the centrifugal separator 16 is platelet-rich plasma, the centrifuge outlet sensor M1 may be configured to determine the platelet concentration of the platelet-rich plasma. The centrifuge outlet sensor M1 may detect the one or more properties of a fluid by optically monitoring the fluid as it flows through tubing of the fluid flow circuit 12 or by any other suitable approach. The controller 18 may receive signals from the centrifuge outlet sensor M1 that are indicative of the one or more properties of fluid flowing out of the centrifugal separator 16 and use the signals to optimize the separation procedure based upon that property or properties, as will be described in greater detail herein.

The illustrated fluid separation device 10 further optionally includes a spinner outlet sensor M2, which accommodates tubing of a fluid flow circuit 12 that flows a separated fluid component out of a spinning membrane separator 26 of the fluid flow circuit 12.

The illustrated fluid separation device 10 also optionally includes an air detector M3 (e.g., an ultrasonic bubble detector), which accommodates tubing of the fluid flow circuit 12 that flows fluid to a recipient or container. It may be advantageous to prevent air from reaching a recipient or container, so the air detector M3 may transmit signals to the controller 18 that are indicative of the presence or absence of air in the tubing. If the signal is indicative of air being present in the tubing, the controller 18 may initiate an alarm or error condition to alert an operator to the condition and/or to take corrective action to prevent the air from reaching the recipient or container (e.g., by reversing the flow of fluid through the tubing or diverting flow to a vent location).

The generally vertical portion 24 of the case 18 may include a plurality of weight scales W1-W6 (six are shown, but more or fewer may be provided), each of which may support one or more fluid containers F1-F8 of the fluid flow circuit 12 (FIG. 6). The containers F1-F8 receive a fluid to be separated, fluid components separated during processing, or intravenous fluids or additive fluids. Each weight scale W1-W6 transmits to the controller 18 a signal that is indicative of the weight of the fluid within the associated container F1-F8 to track the change of weight during the course of a procedure. This allows the controller 18 to process the incremental weight changes to derive fluid processing volumes and flow rates and subsequently generate signals to control processing events based, at least in part, upon the derived processing volumes. For example, the controller 18 may diagnose leaks and obstructions in the fluid flow circuit 12 and alert an operator.

The illustrated case 20 is also provided with a plurality of hooks or supports H1 and H2 that may support various components of the fluid flow circuit 12 or other suitably sized and configured objects.

The Controller

The fluid separation device 10 includes a controller 18, which is suitably configured and/or programmed to control operation of the fluid separation device 10. In one embodiment, the controller 18 comprises a main processing unit (MPU), which can comprise, e.g., a Pentium™ type microprocessor made by Intel Corporation, although other types of conventional microprocessors may be used. In one embodiment, the controller 18 may be mounted inside the generally vertical portion 24 of the case 20, adjacent to or incorporated into an operator interface station (e.g., a touchscreen). In other embodiments, the controller 18 and operator interface station may be associated with the generally horizontal portion 22 or may be incorporated into a separate device that is connected (either physically, by a cable or the like, or wirelessly) to the fluid separation device 10.

The controller 18 is configured and/or programmed to execute at least one fluid processing application but, more advantageously, is configured and/or programmed to execute a variety of different fluid processing applications. For example, the controller 18 may be configured and/or programmed to carry out one or more of the following: a double unit red blood cell collection procedure, a plasma collection procedure, a plasma/red blood cell collection procedure, a red blood cell/platelet/plasma collection procedure, a platelet collection procedure, a platelet/plasma collection procedure, and a mononuclear cell collection procedure. Additional or alternative procedures or applications can be included without departing from the scope of the present disclosure.

More particularly, in carrying out any one of these fluid processing procedures or applications, the controller 18 is configured and/or programmed to control one or more of the following tasks: drawing fluid into a fluid flow circuit 12 mounted to the fluid separation device 10 from a source (such as a patient, donor or container), conveying fluid through the fluid flow circuit 12 to a location for separation (i.e., into the spinning membrane separator 26 or the centrifugal separation chamber 36 of the fluid flow circuit 12), separating the fluid into two or more components as desired, and conveying the separated components into storage containers, to a second location for further separation (e.g., into whichever of the spinning membrane separator 26 and centrifugal separation chamber 36 that was not used in the initial separation stage), or to a recipient (which may be the source from which the fluid was originally drawn).

This may include instructing the spinning membrane separator drive unit 14 and/or the centrifugal separator 16 to operate at a particular rotational speed and instructing at least one of the pumps P1-P6 of the pump system to convey fluid through a portion of the fluid flow circuit 12 at a particular flow rate. Hence, while it may be described herein that a particular component of the fluid separation device 10

(e.g., the spinning membrane separator drive unit 14 or the centrifugal separator 16) performs a particular function, it should be understood that the component is being controlled by the controller 18 to perform that function.

For procedures that call for the use of both the centrifugal separator 16 and the spinning membrane separator drive unit 14, a properly programmed controller 18 is especially important to coordinate the operation of these two components, along with the other components of the fluid separation device 10, to ensure that flow to and from the centrifugal separator 16 and spinning membrane separator drive unit 14 is at the proper level and that the components are functioning properly to process the fluid circulating through the fluid flow circuit 12.

Before, during, and after a procedure, the controller 18 may receive signals from various components of the fluid separation device 10 (e.g., the pressure sensors A1-A4) to monitor various aspects of the operation of the fluid separation device 10 and characteristics of the fluid and separated fluid components as they flow through the fluid flow circuit 12. If the operation of any of the components and/or one or more characteristics of the fluid or separated fluid components is outside of an acceptable range, then the controller 18 may initiate an alarm or error condition to alert the operator and/or take action to attempt to correct the condition. The appropriate corrective action will depend upon the particular error condition and may include action that is carried out with or without the involvement of an operator.

For example, the controller 18 may include an interface control module, which receives signals from the spectrometer 54 of the interface monitoring system 50. The signals that the controller 18 receives from the spectrometer 54 are indicative of the position of an interface between the separated blood components within the centrifugal separation chamber 36. If the controller 18 determines that the interface is in the wrong position, then it can issue commands to the appropriate components of the fluid separation device 10 to modify their operation so as to move the interface to the proper position. For example, the controller 18 may instruct one of the pumps P1-P6 to cause blood to flow into the centrifugal separation chamber 36 at a different rate and/or for a separated blood component to be removed from the centrifugal separation chamber 36 at a different rate and/or for the centrifugal separation chamber 36 to be spun at a different speed by the centrifugal separator 16. A particular protocol carried out by the interface control module in adjusting the position of the interface within the centrifugal separation chamber 36 will be described in greater detail with respect to an exemplary centrifugal separation chamber 36.

If provided, an operator interface station associated with the controller 18 allows the operator to view on a screen or display (in alpha-numeric format and/or as graphical images) information regarding the operation of the system. The operator interface station also allows the operator to select applications to be executed by the controller 18, as well as to change certain functions and performance criteria of the system. If configured as a touchscreen, the screen of the operator interface station can receive input from an operator via touch-activation. Otherwise, if the screen is not a touchscreen, then the operator interface station may receive input from an operator via a separate input device, such as a computer mouse or keyboard. It also is within the scope of the present disclosure for the operator interface station to receive input from both a touchscreen and a separate input device, such as a keypad.

II. The Disposable Fluid Flow Circuit

As for the fluid flow circuit or flow set 12 (FIG. 6), it is intended to be a sterile, single use, disposable item. Before beginning a given fluid separation procedure, the operator loads various components of the fluid flow circuit 12 in the case 20 in association with the fluid separation device 10. The controller 18 implements the procedure based upon preset protocols, taking into account other input from the operator. Upon completing the procedure, the operator removes the fluid flow circuit 12 from association with the fluid separation device 10. The portions of the fluid flow circuit 12 holding the collected fluid component or components (e.g., collection containers or bags) are removed from the case 20 and retained for storage, transfusion, or further processing. The remainder of the fluid flow circuit 12 is removed from the case 20 and discarded.

Figures 9, 10, 11:
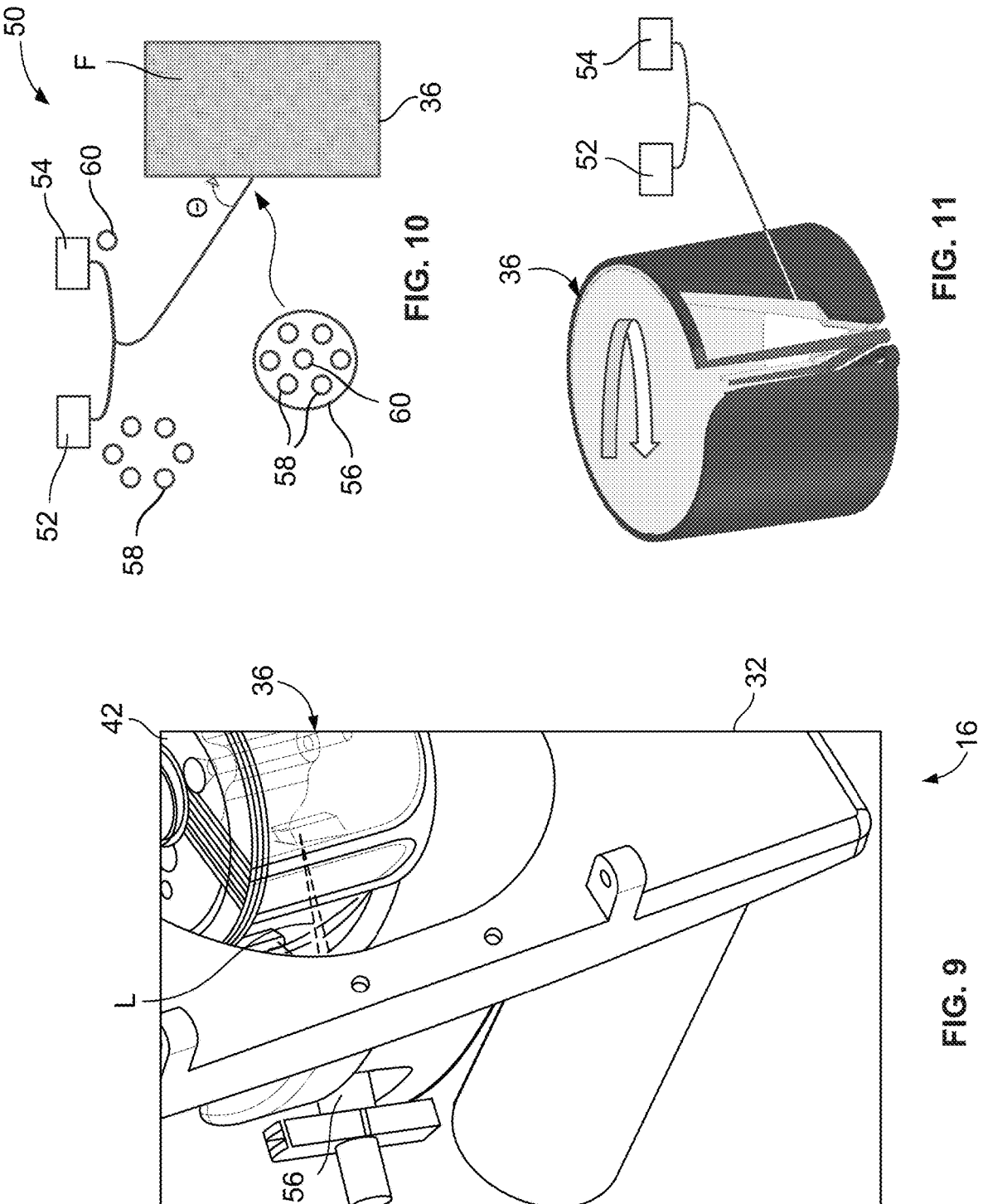
FIG. 9 is a perspective view of the centrifugal separator of FIG. 7, with selected portions thereof broken away to show an optical portion of a color-based interface monitoring system.
FIG. 10 is a schematic diagram of a color-based interface monitoring system having an optical fiber bundle associated with a light source and spectrometer directed at an acute angle relative to a surface of the centrifugal separation chamber and to fluid therein of FIGS. 7 and 9.
FIG. 11 is a schematic diagram of the color-based interface monitoring system of FIG. 10 aimed at an acute angle relative to an interface ramp of a centrifuge fluid path.

A variety of different disposable fluid flow circuits may be used in combination with the blood separation device 10, with the appropriate fluid flow circuit depending on the separation procedure to be carried out using the system. Generally speaking, though, the fluid flow circuit 12 includes a cassette 48 (FIG. 8), to which the other components of the fluid flow circuit 12 are connected by flexible tubing. The other components may include a plurality of fluid containers F1-F8 (for holding fluid to be processed, a separated fluid component, an intravenous fluid, or an additive solution, for example), one or more fluid source access devices (e.g., a connector for accessing blood within a fluid container), and a spinning membrane separator 26 and/or a centrifugal separation chamber 36 (FIGS. 7 and 9).

Cassette and Tubing

The cassette 48 (FIG. 8) provides a centralized, programmable, integrated platform for all the pumping and many of the valving functions required for a given fluid separation procedure. In one embodiment, the cassette 48 is similarly configured to the cassette of U.S. Pat. No. 5,868,696, but is adapted to include additional components (e.g., more tubing loops T1-T6) and functionality.

In use, the cassette 48 is mounted to the cassette station 62 of the fluid separation device 10, with a flexible diaphragm of the cassette 48 placed into contact with the cassette station 62. The flexible diaphragm overlays an array of interior cavities formed by the body of the cassette 48. The different interior cavities define sensor stations S1-S4, valve stations C1-C9, and a plurality of flow paths. The side of the cassette 48 opposite the flexible diaphragm may be sealed by another flexible diaphragm or a rigid cover, thereby sealing fluid flow through the cassette 48 from the outside environment.

Each sensor station S1-S4 is aligned with an associated pressure sensor A1-A4 of the cassette station 62, with each pressure sensor A1-A4 capable of monitoring the pressure within the associated sensor station S1-S4. Each valve station C1-C9 is aligned with an associated valve V1-V9, and may define one or more ports that allow fluid communication between the valve station C1-C9 and another interior cavity of the cassette 48 (e.g., a flow path). As described above, each valve V1-V9 is movable under command of the controller 18 to move between a plurality of positions (e.g., between a retracted or lowered position and an actuated or raised position) to selectively contact the valve stations C1-C9 of the cassette 48. In the actuated position, a valve V1-V9 engages the associated valve station C1-C9 to close one or more of its ports to prevent fluid flow therethrough. In the retracted position, a valve V1-V9 is disengaged from the associated valve station C1-C9 (or less forcefully contacts the associated valve station C1-C9 than when in the actuated position) to open one or more ports associated with the valve station C1-C9, thereby allowing fluid flow therethrough.

As described, a plurality of tubing loops T1-T6 extend from the side surface of the cassette 48 to interact with pumps P1-P6 of the fluid separation device 10. In the illustrated embodiment, six tubing loops T1-T6 extend from the cassette 48 to be received by a different one of six pumps P1-P6, but in other embodiments, a procedure may not require use of all of the pumps P1-P6, in which case the cassette 48 may include fewer than six tubing loops. The different pumps P1-P6 may interact with the tubing loops T1-T6 of the cassette 48 to perform different tasks during a separation procedure, but in one embodiment, a different one of the pumps P1-P6 may be configured to serve as an anticoagulant pump P1, a source pump P2, a saline pump P3, a spinner pump P4, a red blood cell pump P5, and an additive pump P6. Certain procedures may require fewer than all of the sensor stations, valve stations, and/or tubing loops illustrated in the exemplary cassette 48 of FIG. 8, such that it should be understood that the cassettes of different fluid flow circuits 12 may be differently configured (e.g., with fewer sensor stations, valve stations, and/or tubing loops) without departing from the scope of the present disclosure.

Additional tubing extends from the side surface of the cassette 48 to connect to the other components of the fluid flow circuit 12, such as the various fluid containers F1-F8, the spinning membrane separator 26, and the centrifugal separation chamber 36. The number and content of the various fluid containers F1-F8 depends upon the procedure for which the fluid flow circuit 12 is used. The tubing connected to the centrifugal separation chamber 36 (which includes one inlet tube and two outlet tubes) may be aggregated into an umbilicus 46 (FIG. 7) that is engaged by the yoke member 44 of the centrifugal separator 16 (as described above) to cause the umbilicus 46 to orbit around and spin or rotate the centrifugal separation chamber 36 during a separation procedure.

Various additional components may be incorporated into the tubing leading out of the cassette 48 or into one of the cavities of the cassette 48. For example, as shown in FIG. 6, a manual clamp 64 may be associated with a line or lines leading to the blood source and/or fluid recipient, a return line filter 66 (e.g., a microaggregate filter) may be associated with a line leading to a fluid recipient, a filter 68 may be positioned upstream of one or more of the fluid containers to remove a substance (e.g., leukocytes) from a separated component (e.g., red blood cells or platelets) flowing into the fluid container, and/or an air trap 70 may be positioned on a line upstream of the centrifugal separation chamber 36.

Centrifugal Separation Chamber

Figure 14:
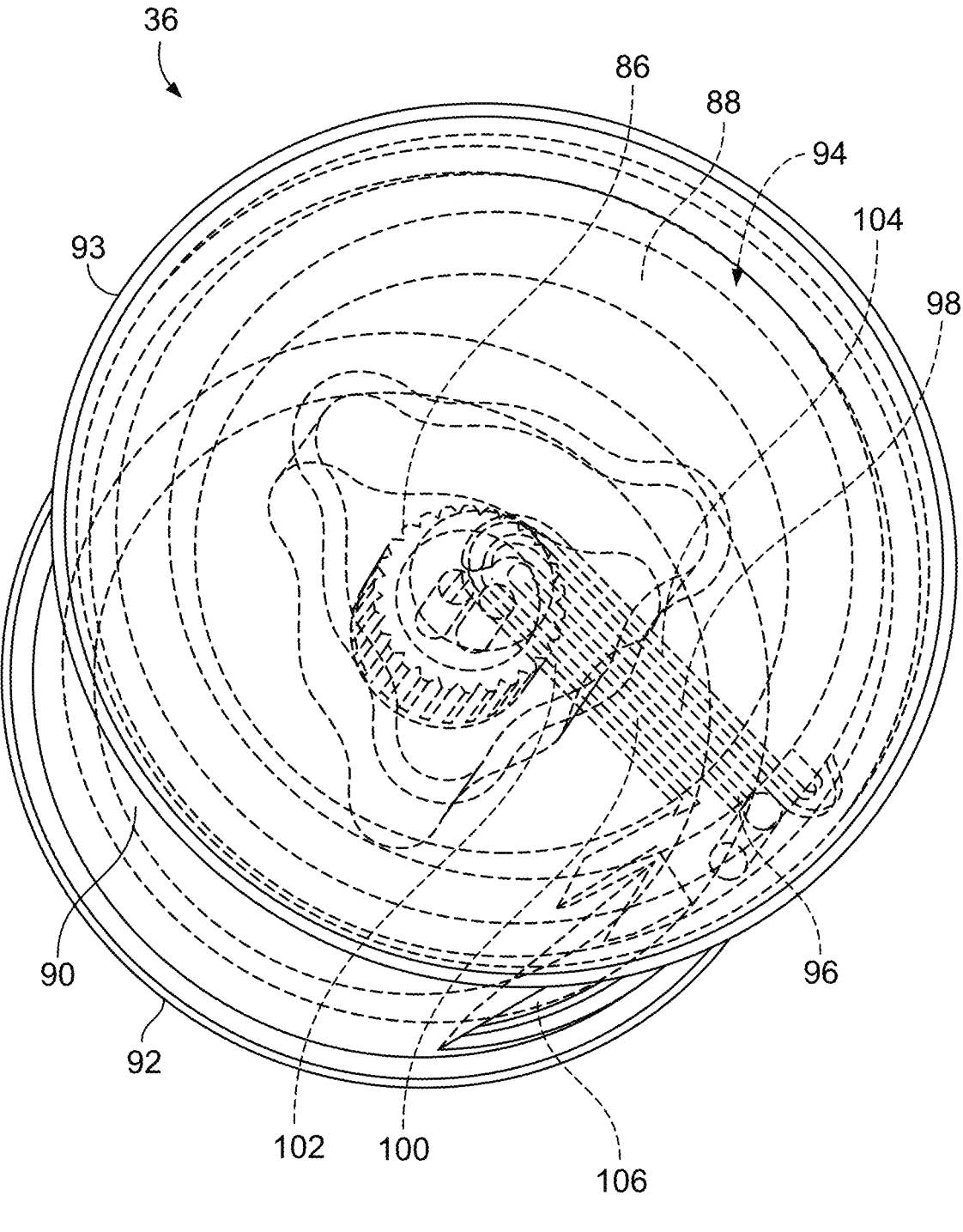
FIG. 14 is a perspective view of an exemplary centrifugal separation chamber of a fluid flow circuit.
Figures 15, 16:
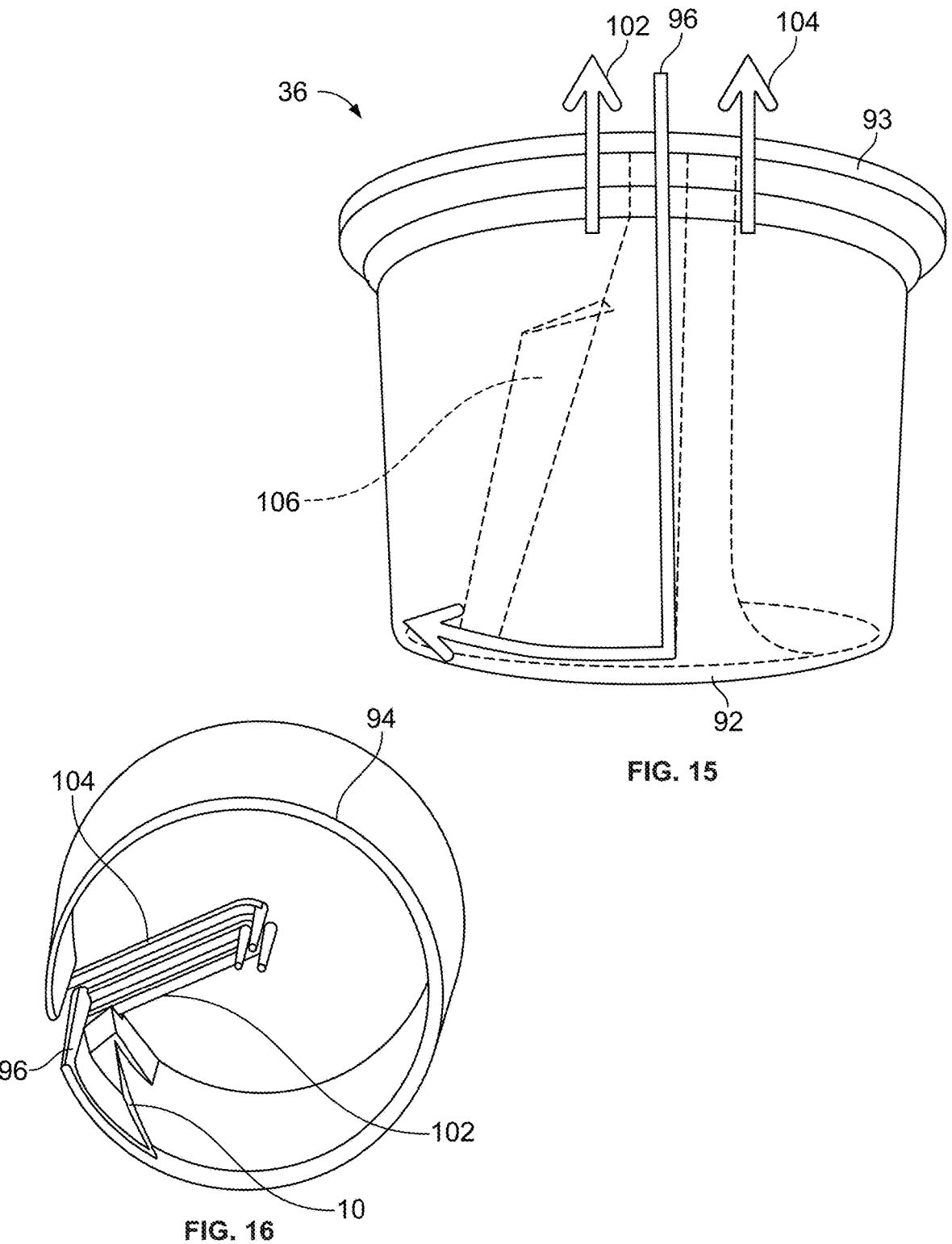
FIG. 15 is a front elevational view of the centrifugal separation chamber of FIG. 14.
FIG. 16 is a bottom perspective view of the fluid flow path through the centrifugal separation chamber of FIG. 14.

An example of the centrifugal separation chamber 36 is shown in further detail in FIGS. 14 and 15, while FIG. 16 illustrates the fluid flow path defined by the centrifugal separation chamber 36. In the illustrated embodiment, the body of the centrifugal separation chamber 36 is pre-formed in a desired shape and configuration (e.g., by injection molding) from a rigid, biocompatible transparent plastic material, such as a non-plasticized medical grade acrylic. All contours, ports, channels, and walls that affect the fluid separation process are preformed in a single, injection molded operation. Alternatively, the centrifugal separation chamber 36 can be formed by separate molded parts, either by nesting cup-shaped subassemblies or two symmetric halves.

The underside of the centrifugal separation chamber 36 includes a shaped receptacle 86 that is suitable for receiving an end of the umbilicus 46 of the fluid flow circuit 12 (FIG. 7). A suitable receptacle 86 and the manner in which the umbilicus 46 may cooperate with the receptacle 86 to deliver fluid to and remove fluid from the centrifugal separation chamber 36 are described in greater detail in U.S. Pat. No. 8,075,468.

The illustrated centrifugal separation chamber 36 has radially spaced apart inner (low-G) and outer (high-G) side wall portions 88 and 90, a bottom or first end wall portion 92, and a cover or second end wall portion 93. The cover 93 comprises a simple flat part that can be easily welded or otherwise secured to the body of the centrifugal separation chamber 36. Because all of the features that affect the separation process are incorporated into one injection molded component, any tolerance differences between the cover 93 and the body of the centrifugal separation chamber 36 will not affect the separation efficiencies of the centrifugal separation chamber 36. The wall portions 88 and 90, the bottom 92, and the cover 93 together define an enclosed, generally annular channel 94 (FIG. 16).

An inlet 96 communicating with the channel 94 is defined between opposing interior radial walls 98 and 100. One of the interior walls 98 joins the outer (high-G) wall portion 90 and separates the upstream and downstream ends of the channel 94. The interior walls 98 and 100 define the inlet passageway 96 of the centrifugal separation chamber 36 which, in one flow configuration, allows fluid to flow from the umbilicus 46 to the upstream end of the channel 94.

The illustrated centrifugal separation chamber 36 further includes first and second outlets 102 and 104, respectively, which may be defined by opposing surfaces of interior radial walls. Both the first and second outlets 102 and 104 extend radially inward from the channel 94 and may be characterized as outlet lines. The first outlet 102 extends radially inward from an opening which, in the illustrated embodiment, is located at the inner side wall portion 88, while the second outlet 104 extends radially inward from an opening that is associated with the outer side wall portion 90. The illustrated first outlet 102 is positioned adjacent to the inlet 96 (near the upstream end of the channel 94), while the second outlet 104 may be positioned at the opposite, downstream end of the channel 94.

The illustrated centrifugal separation chamber 36 further includes first and second outlets 102 and 104, respectively, which may be defined by opposing surfaces of interior radial walls. Both the first and second outlets 102 and 104 extend radially inward from the channel 94 and may be characterized as outlet lines. The first outlet 102 extends radially inward from an opening which, in the illustrated embodiment, is located at the inner side wall portion 88, while the second outlet 104 extends radially inward from an opening that is associated with the outer side wall portion 90. The illustrated first outlet 102 is positioned adjacent to the inlet 96 (near the upstream end of the channel 94), while the second outlet 104 may be positioned at the opposite, downstream end of the channel 94.

III. Centrifugal Separation and Interface Detection Principles

Fluid flowed into the channel 94 separates into an optically dense layer RBC and a less optically dense layer PLS (FIGS. 17-19) as the centrifugal separation chamber 36 is rotated about the rotational axis 38. The optically dense layer RBC forms as larger and/or heavier fluid particles move under the influence of centrifugal force toward the outer (high-G) wall portion 90. If the fluid being separated is blood, the optically dense layer RBC will typically include red blood cells (and, hence, may be referred to herein as the "RBC layer") but, depending on the speed at which the centrifugal separation chamber 36 is rotated, other cellular components (e.g., larger white blood cells) may also be present in the optically dense layer RBC.

If the fluid being separated is blood, the less optically dense layer PLS typically includes a plasma constituent, such as platelet-rich plasma or platelet-poor plasma (and, hence, will be referred to herein as the "PLS layer"). Depending on the speed at which the centrifugal separation chamber 36 is rotated and the length of time that the blood is resident therein, other components (e.g., smaller white blood cells and anticoagulant) also may be present in the less optically dense layer PLS.

In one embodiment, blood introduced into the channel 94 via the inlet 96 will travel in a generally clockwise direction (in the orientation of FIG. 14) as the optically dense layer RBC separates from the less optically dense layer PLS. The optically dense layer RBC continues moving in the clockwise direction as it travels the length of the channel 94 along the outer side wall portion 90, from the upstream end to the downstream end, where it exits the channel 94 via the second outlet 104. The less optically dense layer PLS separated from the optically dense layer RBC reverses direction, moving counterclockwise along the inner side wall portion 88 to the first outlet 102, adjacent to the inlet 96. The inner side wall portion 88 may be tapered inward as it approaches the second outlet 104 to force the plasma liberated at or adjacent to the downstream end of the channel 94 to drag the interface back towards the upstream end of the channel 94, where the lower surface hematocrit will resuspend any platelets settled on the interface.

Figure 17:
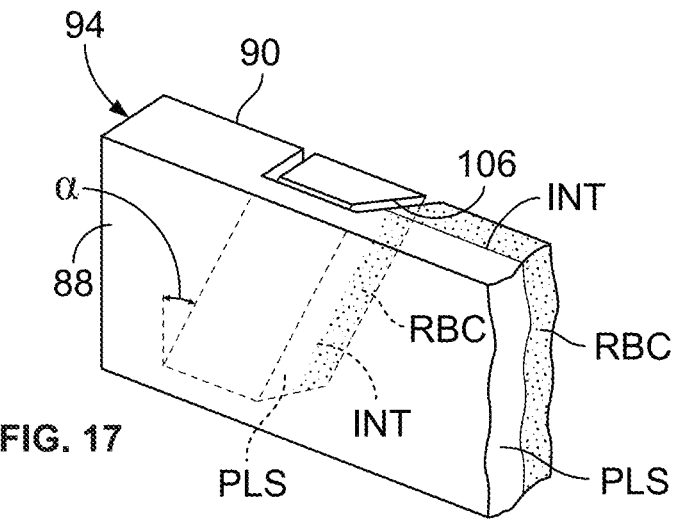
FIG. 17 is an enlarged perspective view of a portion of a channel of the centrifugal separation chamber of FIGS. 14-16, with an interface between separated fluid components being positioned at a (typically) desired position on a ramp defined within the channel.
Figure 18:
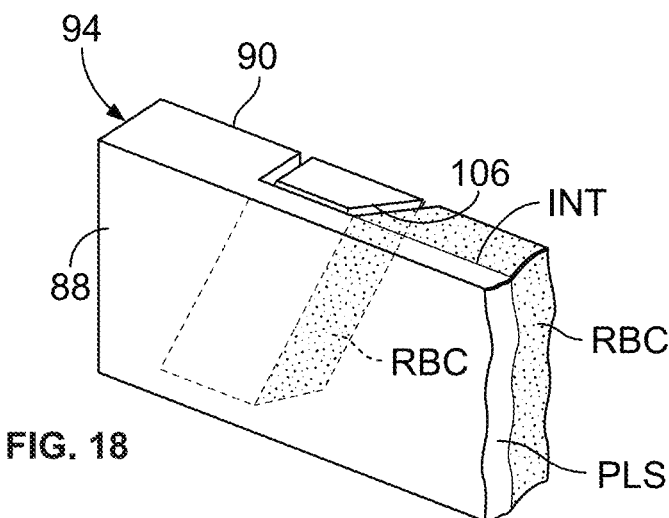
FIG. 18 is an enlarged perspective view of the channel and ramp of FIG. 17, with the interface being at a (typically) undesired high position on the ramp.
Figure 19:
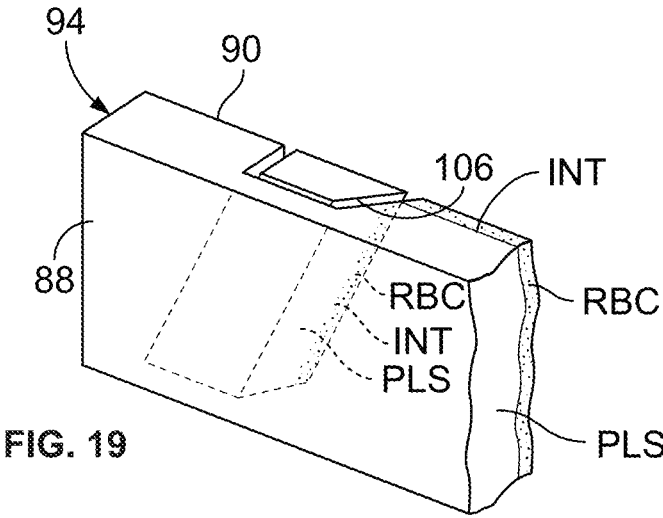
FIG. 19 is an enlarged perspective view of the channel and ramp of FIG. 17, with the interface being at a (typically) undesired low position on the ramp.

The transition between the optically dense layer RBC and the less optically dense layer PLS may be referred to as the interface INT. If the fluid being separated is blood, the interface INT contains mononuclear cells and peripheral blood stem cells. The position of the interface INT within the channel 94 of the centrifugal separation chamber 36 can dynamically shift during fluid processing, as shown in FIGS. 17-19. If the position of the interface INT is too high (that is, if it is too close to the inner side wall portion 88 and the first outlet 102, as in FIG. 18), red blood cells can flow into the first outlet 102, potentially adversely affecting the quality of the low density components (platelet-rich plasma or platelet-poor plasma). On the other hand, if the position of the interface INT is too low (that is, if it resides too far away from the inner wall portion 88, as in FIG. 19), the collection efficiency of the system may be impaired. The ideal or target interface position may be experimentally determined, which may vary depending on any of a number of factors (e.g., the configuration of the centrifugal separation chamber 36, the rate at which the centrifugal separation chamber 36 is rotated about the rotational axis 38, etc.). As will be described herein, it may be advantageous to adjust the position of the interface INT away from the position of FIG. 17 during a separation procedure.

Exemplary Interface Control Using Color-Based Optical Measurements

As described above, the fluid separation device 10 may include a color-based interface monitoring system 50 and a controller 18 with an interface control module to monitor and, as necessary, adjust or correct the position of the interface INT. (As noted previously, the system also optionally may include a centrifuge outlet sensor M1). In one embodiment, the centrifugal separation chamber 36 is formed with a ramp 106 extending from the high-G wall portion 90 at an angle α across at least a portion of the channel 94 (FIGS. 14 and 17-19). The angle α, measured with respect to the rotational axis 38 is about 25° in one embodiment. FIGS. 16-18 show the orientation of the ramp 106 when viewed from the low-G side wall portion 88 of the centrifugal separation chamber 36. Although it describes a flexible separation chamber, the general structure and function of the ramp 106 may be better understood with reference to U.S. Pat. No. 5,632,893, which is hereby incorporated herein by reference. The ramp 106 may be of a different angle and may be positioned at any of a number of locations between the upstream and downstream ends of the channel 94, but in one embodiment, the ramp 106 may be positioned generally adjacent to the first outlet 102, in the path of fluid and/or a fluid component moving from the inlet 96 to the first outlet 102.

The ramp 106 makes the interface INT between the optically dense layer RBC and the less optically dense layer PLS more discernible for detection, displaying the optically dense layer RBC, less optically dense layer PLS, and interface INT for viewing through a light-transmissive portion of the centrifugal separation chamber 36. To that end, the ramp 106 and at least the portion of the centrifugal separation chamber 36 angularly aligned with the ramp 106 may be formed of a light-transmissive material, although it may be advantageous for the entire centrifugal separation chamber 36 to be formed of the same light-transmissive material.

In the illustrated embodiment, the broadband light source 52 of the color-based interface monitoring system 50 is carried by at least one optical fiber 58 of an optical fiber bundle 56, which is secured to a fixture or wall of the centrifuge compartment 32 and oriented to emit a light that is directed toward the surface of the centrifugal separation chamber 36 at an acute angle Θ, as shown in the schematic diagram in FIGS. 10 and 11. The at least one optical fiber 60 of the optical bundle 56 that carries reflected light to the spectrometer 54 is positioned at the same acute angle Θ, so as to light reflected by the fluid in the centrifugal separation chamber 36 when the light L is emitted by the light source 52.

The systems and methods of the present disclosure aim to eliminate the requirement for light transmission through the plasma layer and detection such as via a prism, which can be problematic when a plasma layer becomes less optically clear, such as in the case of lipemic plasm. By instead utilizing a spectrometer to measure the color of the fluid layers via reflectance spectroscopy, or by using any other acceptable color measurement technique, this novel method enables a color-based interface control system 50 to be dependent only on the color of the fluid layers and not optical clarity. Using current transmission-based methods a buffy coat and RBC layer cannot be well distinguished because both contain cells which prevent the transmission of light. However, this color-based method may differentiate a buffy coat layer, which is white in color, from RBCs, which are red in color, which also may be beneficial.

When a light is shined into a sample of blood (or any material in general) the light may be absorbed, the light may be transmitted through the sample typically scattering as it propagates, or the light may be diffusely scattered backward. Blood and blood components with cells, which are considered turbid media, are characterized by low to moderate absorption and strong scattering properties. The intensity of the light that is reflected or transmitted by a blood sample is determined by the optical properties of the fluid, particularly the scattering coefficient, absorption coefficient, and the anisotropic factor. When a visible broadband incident light source (e.g., wavelengths from 400 to 700 nm) is applied, the wavelengths/colors that are not absorbed, and thus reflected or transmitted, is dependent on the absorption coefficient of the particles in the fluid.

The wavelengths of each layer of the separated fluid components may be determined by any suitable approach without departing from the scope of the present disclosure. In the example embodiment, the dominant wavelength of a particular layer of a separated fluid component in the centrifuge may be determined using a broadband light source 52 (such as Thorlabs Stabilized Tungsten-Halogen Light Source, Part Number SLS201L, 360-2600 nm, or a suitable alternative), optical fibers 58, 60 (such as Thorlabs 200 um Fiber Bundle Reflection Probe, Part Number RP20 or a suitable alternative), and a spectrometer 54 (such as Thorlabs Compact CCD Spectrometer, Part Number CCS200, 200-1000 nm, or a suitable alternative). The light source shall contain at a minimum all wavelengths in the visible range (approximately 400-700 nm) but may contain wavelengths above or below this range as well. As noted previously, a schematic diagram of the set-up as applied is shown in FIG. 10. It will be appreciated that the device for measuring the dominant wavelength/color of the reflected light R, such as the spectrometer 54, may be configured for measurement and wavelength differentiation of at least a portion of the reflected light R received or it may pass a signal along to the controller 18 to make such determinations.

As indicated in FIG. 10, the optical fiber bundle 56, which may include at least one optical fiber 58 to carry light from the light source 52 and at least one optical fiber 60 to carry reflected light R to the spectrometer 54, in this example has a cross-section that includes seven 200 um fibers, six of which are optical fibers 58 arranged around a periphery of the optical fiber bundle 56 and carry incident light from the broadband light source 52 to the fluid sample F, and one centrally located optical fiber 60 that carries light reflected by the fluid sample F to the spectrometer 54 for wavelength/color measurement. While the optical fiber 60 is centrally located relative to ring-shaped configuration of the optical fibers 58, it will be appreciated that at a minimum only one optical fiber 58 is required to transfer light L from the light source 52 to the fluid sample F, and one optical fiber 60 to transfer reflected light R from the sample fluid F to the spectrometer 54.

The fiber bundle 56 advantageously is placed at a selected acute angle Θ with respect to the sample fluid F in the centrifugal separation chamber 36 to minimize the amount of specular reflectance from the surface of the centrifugal separation chamber 36 in which the color of the fluid F measured. If Θ were equal to 90°, a significant amount of specular reflectance from the container surface would go directly back in the direction of the fiber bundle 56, and thus, the measured light would contain mostly the spectrum of the light L from the light source 52 itself and not the spectrum reflected by the sample fluid F. If Θ were equal to 0°, there would not be any light incident on the sample fluid F. Accordingly, an acute angle between 0° and 90° should be applied. It should be noted that it was determined experimentally that 45° is an optimum angle that produces the most sensitive color measurements, although it appears that any angle from 30° to 60° may be acceptable.

The light that enters the sample fluid F will be absorbed and scattered based on the unique optical properties of the sample. The reflected light R that is reflected directly back toward the optical fiber bundle 56 will be captured by the optical fiber 60 and transported to the spectrometer 54 for quantification and wavelength differentiation (color measurement), consistent with FIGS. 12 and 13.

The method of this disclosure takes advantage of the color measurement technique explained above to measure the dominant wavelength of the respective layers of the separated fluid components within the sample fluid F in the centrifugal separation chamber 36 during operation of the centrifugal separator 16. The dominant wavelength measurements are combined with duration or color time measurements to be used in controlling the position of the interface INT between layers, such as the plasma layer PSL having a first color and red blood cell layer RBC having a second color. The color-based interface monitoring system 50 utilizes the broadband light source 52 and spectrometer 54, with the fiber bundle 56 in a configuration directed or aimed toward the location of the chamber ramp 106 to enable color measurement of the layers of the sample fluid F each time the chamber ramp 106 rotates past the optical fiber bundle 56, as depicted in FIG. 11.

Figure 20:
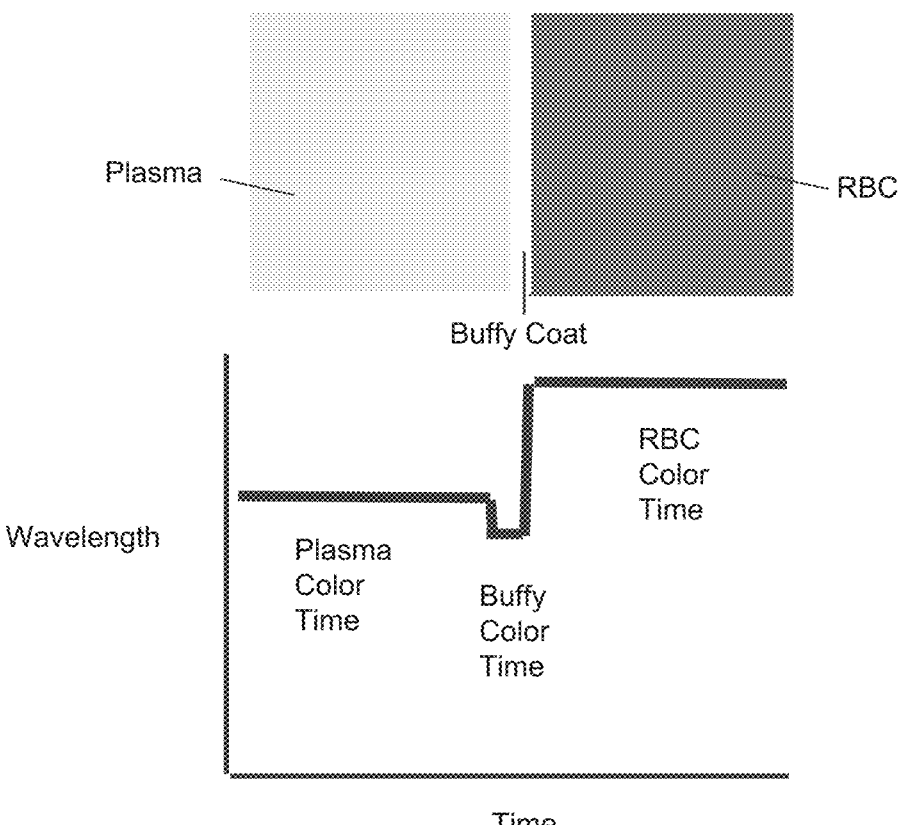
FIG. 20 is a schematic representation of a measurement of different dominant wavelengths of color of layers of fluid over time.

As the ramp 106 in the centrifugal separation chamber 36 rotates past the location where the optical fiber bundle 56 is directed, the spectrometer 54 will receive reflected light R and measure different dominant wavelengths of color over time, exemplified in FIG. 20. The duration over which any particular dominant wavelength is measured can be compared to a pre-determined target duration to control the thickness of the layers in the sample fluid F, and thus, the interface position(s) between the layers. The Error Signal of the color-based interface monitoring system 50 now becomes the difference between the time measurement of color or duration as a color time (e.g., Plasma Color Time) and the targeted time for color (e.g., a setpoint for Plasma Target Time). The measurement of color may take place upon each rotation of the centrifugal separation chamber 36, or in pre-determined intervals.

Exemplary Interface Detection and Control

In the example shown, during separation of blood within the channel 94, the light L from the light source 50 travels through a light-transmissive portion of the outer side wall portion 90 and toward the ramp 106 to intersect the separated blood components thereon when the ramp 106 has been rotated into the initial path of the light L. After passing through the ramp 106, the light continues through the channel 94 and the fluids in the channel 94. At least a portion of the light L (i.e., the portion reflected by the fluids toward the optical fiber bundle 56) exits the channel 94 and is carried by the at least one optical fiber 60 to the spectrometer 54. Thus, it will be seen that the light L reaches the spectrometer 54 after exposure to the color of the respective fluids, such as the separated blood components, and reflection therefrom. Requiring color measurement of the reflected light R by the spectrometer 54 upon rotation of the centrifugal separation chamber 36 effectively senses the position of the different separated layers of fluid, which may improve monitoring and correction of the interface position.

The spectrometer 54 of the color-based interface monitoring system 50 generates a signal that is transmitted to the interface control module of the controller 18, which can determine the position of the interface INT on the ramp 106. In one embodiment, the position of the interface INT is associated with distinguishing between the colors of the layers of separated components in the centrifugal separation chamber 36.

In such an embodiment, as the ramp 106 is rotated into the path of the light L from the light source 52, the light L will first encounter the portion of the ramp 106 that is positioned closest to the inner side wall portion 88 (i.e., the section of the ramp 106 that most restricts the channel 94), as shown in FIG. 14. As described above, the less optically dense layer PLS having a first color will be positioned adjacent to the inner side wall portion 88 as it separates from the optically dense layer RBC having a second color, such that the fluid displayed on this radially innermost section of the ramp 106 (i.e., the fluid present in the channel 94 between the ramp 106 and the inner side wall portion 88) will be the less optically dense layer PLS tending to have the first color. Some of the light is reflected backward from the layer PLS having the first color to the optical fiber bundle 56 and through the at least one optical fiber 60 to the spectrometer 54. The spectrometer measures the dominant wavelength/color of the reflected light R to determine the color of the fluid. This causes the spectrometer 54 to send a signal to the controller 18. Depending on the measured color and duration or color time of the fluid layer, the controller may adjust the pump system to adjust the thick ness of the measured layer and thereby control the position of the interface position between the layers.

Further rotation of the ramp 106 through the path of light L from the light source 52 exposes the light L to portions of the ramp 106 that are increasingly spaced from the inner side wall portion 88 (i.e., the light L travels through portions of the channel 94 that are less restricted by the ramp 106 as the ramp 106 is rotated through the path of the light L). Up until the time that the interface INT on the ramp 106 is rotated into the path of the light L, the only fluid in the channel 94 that the light L will have passed through will be the less optically dense layer PLS having the first color, such that a generally uniform dominant wavelength or color of reflected light R is received by the spectrometer 54. Accordingly, the output of the spectrometer 54 will be generally uniform while the ramp 106 passes through the path of the light L before being exposed to the interface INT. The controller 18 may be programmed and/or configured to consider a signal that deviates from a particular signal level for purposes of calculating the duration of color time (duration of time a dominant wavelength is measured) of the signal. The controller 18 will treat a greater deviation of the signal as representing the end of the particular signal for purposes of calculating the duration of color time of the signal for the color of the particular fluid layer being measured.

Just after the interface INT has been rotated into the path of light L from the light source 52, the light L will begin to encounter the optically dense layer RBC having the second color in the channel 94. As described above, the optically dense layer RBC will be positioned adjacent to the outer side wall portion 90 as it separates from the less optically dense layer PLS, such that the optically dense layer RBC will not be displayed on the ramp 106 until the ramp 106 is spaced a greater distance away from the inner side wall portion 88.

The dominant wavelength of the light reflected by the optically dense layer RBC and carried by the optical fiber 60 to the spectrometer will provide for a color measurement of the second color, which will differ from the wavelength/color measurement of the first color associated with the layer PLS, and generate a different signal. The controller 18 may be programmed and/or configured to recognize this different signal as representing the presence of the optically dense layer RBC having the second color on the ramp 106 (and in the portion of the channel 94 being traversed by the light L) and to treat this differentiated signal as the end point of the signal generated by the light spectrometer 54 while light is reflected by the less optically dense layer PLS having the first color in the channel 94.

Thus, the duration of color time of the signal from the spectrometer 54 to the controller 18 (i.e., the time during which the reflected light R is of a particular color with respect to the less optically dense layer PLS in the channel 94) is determined by the percentages of the ramp 106 that are occupied by the less optically dense layer PLS having the first measured color and the optically dense layer RBC having the second measured color. Accordingly, a greater duration of a color time of the signal from the spectrometer 54 to the controller 18 that is associated with the measured color of the less optically dense layer PLS indicates that the layer is occupying a larger portion of the ramp 106, and in turn will be indicative of a thinner optically dense layer RBC having the second measured color on the ramp 106 (and in the channel 94). Conversely, a signal from the light spectrometer 54 to the controller 18 having a lesser duration of a color time of the signal is associated with the less optically dense layer PLS having the first measured color occupying a smaller portion of the ramp 106 will be indicative of a thicker optically dense layer RBC having the second measured color on the ramp 106 (and in the channel 94). Indeed, each layer may be directly measured and generate a respective duration of a color time of the signal indicative of its thickness.

Comparing the duration of time of the dominant wavelength measurements associated with each color of fluid present on the ramp 106 will indicate the percentage of the ramp 106 that is occupied by the less optically dense layer PLS having the first color and by the optically dense layer RBC having the second color, which information the controller 18 may use to determine the position of the interface INT within the channel 94.

Thus, a fluid separation device 10 is provided and includes a centrifugal separator 16 configured to receive a centrifugal separation chamber 36 of a disposable fluid flow circuit 12. A pump system (such as the pump system having a plurality of pumps P1-P6) is configured to convey a fluid F into the centrifugal separation chamber 36, and to remove a separated fluid component (such as platelet-rich plasma) from the centrifugal separation chamber 36. An outlet (such as outlet 102 or 104) is associated with the centrifugal separation chamber 36 for removing at least a portion of the separated fluid component from the centrifugal separation chamber 36. A color-based interface monitoring system is configured to determine an interface position INT between separated fluid components continuously flowing through the centrifugal separation chamber 36 based on color measurements of layers of the fluid during a centrifugal separation procedure.

The system 10 further includes a controller 18, which is configured to control the pump system to convey a fluid F into the centrifugal separation chamber 36, control the centrifugal separator 16 to separate the fluid F in the centrifugal separation chamber 36 into layers of separated fluid components with the interface INT located between the layers of separated fluid components. The controller 18 is further is configured to measure a color of each layer of the respective separated fluid components via a dominant wavelength of reflected light R, calculate a duration as a color time for each dominant wavelength associated with the respective layers of separated fluid components, set a predetermined target color time as a setpoint for each layer, calculate an error signal, and utilize the error signal and calculate proportional-integral-derivative terms and a control signal that changes a pump system setting so as to adjust the interface position.

It should be understood that this system for controlling the position of the interface INT is merely exemplary and that differently configured and/or functioning systems may be employed without departing from the scope of the present disclosure.

Adjustment of Target Interface Position

It will be appreciated that the separation procedure is dynamic and to attain an enhanced result may be subject to adjustment throughout the procedure. Thus, while the foregoing description is useful in determining the position of an interface INT, the interface position will be subjected to adjustment as the system and method progress through a procedure. Accordingly, for example, the duration of a measured wavelength, target color time as a setpoint, error signals and flow rates are not static throughout a separation procedure and may be subject to change.

Figure 21:
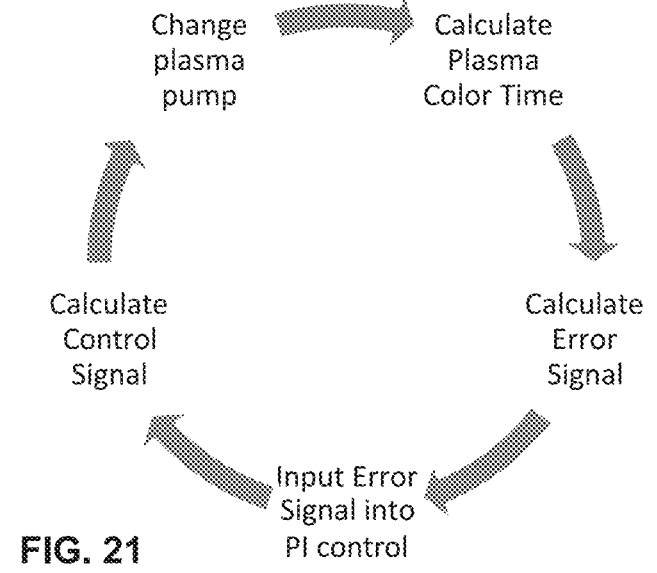
FIG. 21 is a diagram of a control loop for the color measurement method for a system controller that seeks to calculate a Plasma Control Time, then calculate an Error Signal, then input the Error Signal into the PI control, then calculate a Control Signal to then change the plasma pump.
Figure 22:
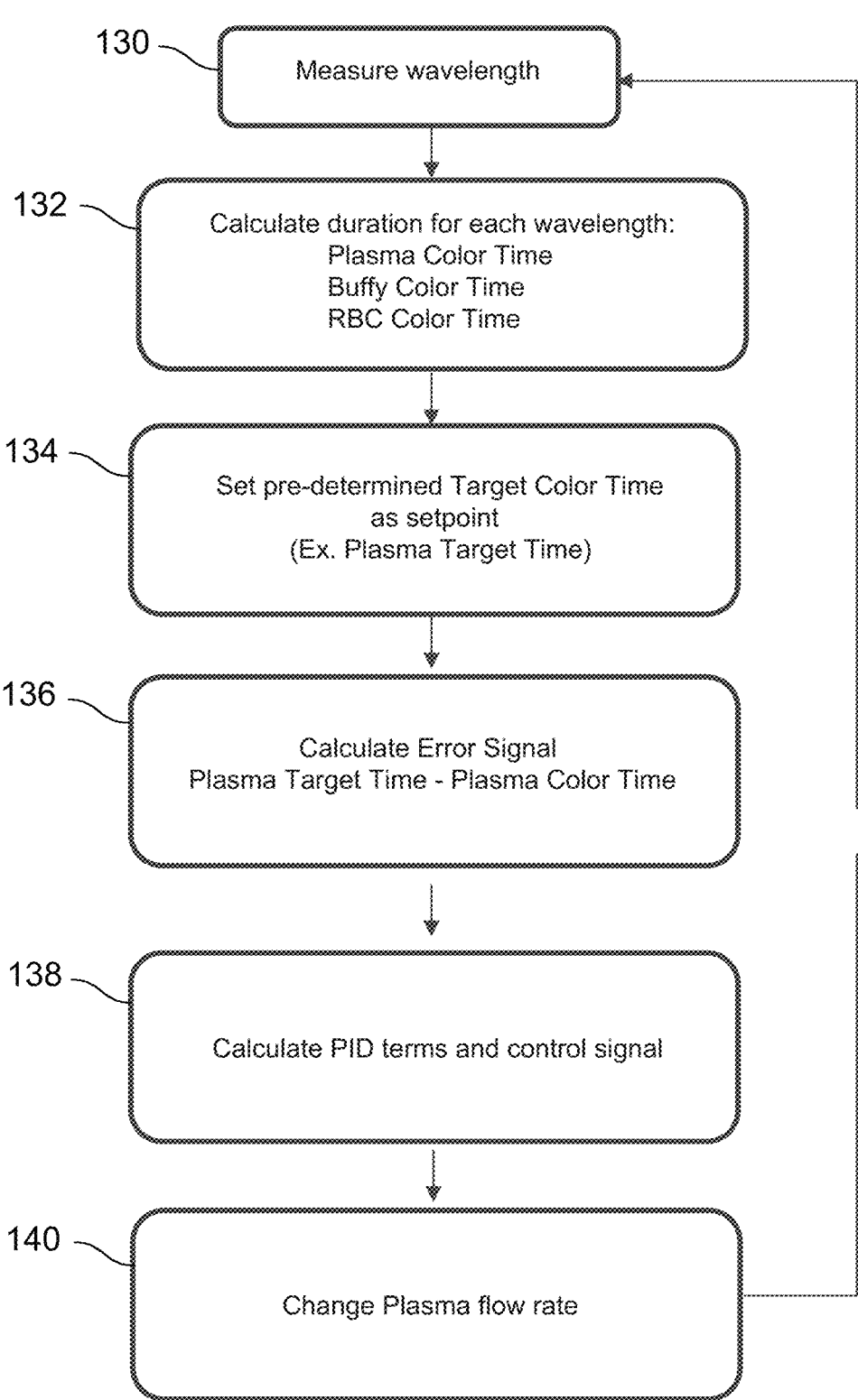
FIG. 22 is a logic flowchart utilized in conjunction with the control loop of FIG. 21 in the color measurement method.

The logic flowchart and method control loop shown in FIGS. 21 and 22 show an exemplary approach to continuous adjustment of a setpoint. A separation procedure begins with fluid F being conveyed into the centrifugal separation chamber 36 of a fluid flow circuit 12 positioned within the centrifuge or centrifugal separator 16. The fluid F is separated into at least two fluid components, with the separated fluid components continuously flowing through the centrifugal separation chamber 36, with an interface INT positioned therebetween. The separation procedure begins with an initial setpoint or target position of the interface. The initial target position may be experimentally determined and based on the separation procedure selected by an operator or may be otherwise selected or determined. For example, in the case of a blood separation procedure in which red blood cells (as a layer RBC having a first color dominant wavelength) are separated from platelet-rich plasma (as a layer PLS having a different second color dominant wavelength), the initial target position of the interface INT may be the position at which the platelet concentration of the platelet-rich plasma will be sufficiently high without red blood cells tending to exit the centrifugal separator 16 with the platelet-rich plasma.

The separated fluid components flow out of the centrifugal separation chamber 36, such as at least a portion of one of the separated fluid components passing through outlet 102 or 104. As represented in FIG. 22, the system may continue to operate and apply a method of adjusting a target position of an interface INT between the separated fluid components that are continuously flowing through the centrifuge 16. The method includes separating fluid F in a centrifuge 16 into layers of separated fluid components with an interface INT between the separated layers. As shown at 130, the method includes measuring a color dominant wavelength of each layer. Next, at 132 the method includes calculating a duration as a color time for each measured dominant wavelength relative to each layer. At 134, the method includes setting a predetermined target color time as a set point for a selected layer. At 136, the method continues by calculating an error signal equal to the target color time minus the calculated color time for the selected layer. At 138, the method includes calculating proportional-integral-derivative terms and a control signal. At 140, the method further includes using the control signal to change a flow rate of the separated fluid components through the centrifuge to adjust the interface position. As shown in FIG. 22, it is contemplated that this method may be repeated to account for and adapt to the continued processing and separation of the fluid in the centrifugal separation chamber 36.

Regardless of the particular configuration of the centrifuge in the present disclosure, a separation procedure begins with fluid being conveyed into the centrifugal separation chamber 36 of a fluid flow circuit 12 positioned within the centrifuge or centrifugal separator 16. The fluid is separated into at least two fluid components, with the separated fluid components continuously flowing through the centrifugal separation chamber 36, with an interface positioned therebetween. The separation procedure begins with an initial setpoint or target position of the interface.

Aspects

Aspect 1. A fluid separation device comprising: a centrifugal separator configured to receive a centrifugal separation chamber of a disposable fluid flow circuit; a pump system configured to convey a fluid into the centrifugal separation chamber, and to remove a separated fluid component from the centrifugal separation chamber; an outlet associated with the centrifugal separation chamber for removing at least a portion of the separated fluid component from the centrifugal separation chamber; a color-based interface monitoring system configured to determine an interface position between separated fluid components continuously flowing through the centrifugal separation chamber based on color measurements of layers of the fluid during a centrifugal separation procedure; and a controller configured to: control the pump system to convey a fluid into the centrifugal separation chamber; control the centrifugal separator to separate the fluid in the centrifugal separation chamber into layers of separated fluid components with the interface located between the layers of separated fluid components; measure a color of each layer of the respective separated fluid components via a dominant wavelength of reflected light; calculate a duration for each dominant wavelength associated with the respective layers of separated fluid components; set a predetermined target color time as a setpoint for each layer; calculate an error signal; and utilize the error signal and calculate proportional-integral-derivative terms and a control signal that changes a pump system setting so as to adjust the interface position.

Aspect 2. The fluid separation device of Aspect 1, wherein the color-based interface monitoring system further comprises a broadband light source and a spectrometer.

Aspect 3. The fluid separation device of Aspect 2, wherein the broadband light source includes a minimum of all wavelengths in a visible range of approximately 400-700 nm.

Aspect 4. The fluid separation device of any of Aspects 2-3, wherein the broadband light source further comprises at least one optical fiber.

Aspect 5. The fluid separation device of any of Aspects 2-4, wherein the broadband light source and spectrometer are configured to be connected to an optical fiber bundle including at least one optical fiber which carries light from the broadband light source to the fluid in the centrifugal separation chamber and at least one optical fiber that carries light reflected by the fluid in the centrifugal separation chamber to the spectrometer.

Aspect 6. The fluid separation device of Aspect 5, wherein the optical fiber bundle includes a plurality of optical fibers that carry light from the broadband light source and are arranged around the at least one optical fiber that carries reflected light to the spectrometer.

Aspect 7. The fluid separation device of Aspect 5, wherein the optical fibers of the optical fiber bundle are placed at a selected acute angle relative to a surface of the centrifugal separation chamber containing the fluid being processed.

Aspect 8. The fluid separation device of Aspect 7, wherein the selected acute angle is an angle between 30° and 60°.

Aspect 9. The fluid separation device of Aspect 7, wherein the selected acute angle is 45°.

Aspect 10. The fluid separation device of Aspect 1, wherein the error signal for a selected layer is equal to the target color time minus the calculated color time for the selected layer.

Aspect 11. The fluid separation device of any of Aspects 1-10, wherein the fluid comprises anticoagulated whole blood, the interface is between red blood cells and plasma, and the separated fluid component is the plasma.

Aspect 12. The fluid separation device of any of Aspects 1-10, wherein the fluid separation device is configured to process blood to separate at least one cellular component from plasma.

Aspect 13. The fluid separation device of any of Aspects 1-12, wherein the controller is further configured to repeatedly: measure a color of each layer of the respective separated fluid components via a dominant wavelength of reflected light; calculate a duration as a color time for each measured dominant wavelength associated with the respective layers of separated fluid components; set a predetermined target color time as a setpoint for the interface position; calculate an error signal; and utilize the error signal and calculate proportional-integral-derivative terms and a control signal that changes a pump system setting so as to adjust the interface position.

Aspect 14. The fluid separation device of Aspects 1-10, wherein the fluid comprises anticoagulated whole blood, the interface is between red blood cells and platelet-rich plasma, the separated fluid component is the platelet-rich plasma, and the controller is further configured to repeatedly complete a routine of calculating the duration as a color time for the measured dominant wavelength of the platelet-rich plasma layer, calculating an error signal, utilizing the error signal to calculate proportional-integral-derivative terms and to calculate a control signal, and using the calculated control signal to change the pump system setting to adjust the interface position.

Aspect 15. A method of adjusting a target position of an interface between separated fluid components continuously flowing through a centrifuge, comprising: separating fluid in a centrifuge into layers of separated fluid components with an interface between the separated layers; measuring a color dominant wavelength of each layer; calculating a duration as a color time for each measured dominant wavelength relative to each layer; setting a predetermined target color time as a set point for a selected layer; calculating an error signal equal to the target color time minus the calculated color time for the selected layer; calculating proportional-integral-derivative terms and a control signal; and using the control signal to change a flow rate of the separated fluid components through the centrifuge to adjust the interface position.

Aspect 16. The method of Aspect 15, wherein the control signal further comprises a signal for operating a pump system that controls the flow rate of the separated fluid components.

Aspect 17. The method of Aspect 15, further comprising repeating said steps of: measuring a color dominant wavelength of each layer; calculating a duration as a color time for each measured dominant wavelength relative to each layer; setting a predetermined target color time as a set point for a selected layer; calculating an error signal equal to the target color time minus the calculated color time for the selected layer; calculating proportional-integral-derivative terms and a control signal; and using the control signal to change a flow rate of the separated fluid components through the centrifuge to adjust the interface position.

Aspect 18. The method of Aspect 15, further comprising wherein the fluid comprises anticoagulated whole blood, the interface is between red blood cells and platelet-rich plasma, and the separated fluid component is platelet-rich plasma.

Aspect 19. The method of Aspect 18, further comprising measuring the dominant wavelength of the platelet-rich plasma layer, calculating the duration as a color time for the measured dominant wavelength of the platelet-rich plasma layer, setting a predetermined target color time for the platelet-rich plasma layer, calculating an error signal equal to the platelet-rich plasma layer target color time minus the platelet-rich plasma layer calculated color time, utilizing the error signal to calculate proportional-integral-derivative terms and to calculate a control signal, and using the calculated control signal to change a flow rate of the separated fluid components continuously flowing through the centrifuge to adjust the interface position.

Aspect 20. The method of Aspect 19, wherein the control signal further comprises a signal for operating a pump system that controls the flow rate of the separated fluid components continuously flowing through the centrifuge.

Aspect 21. The method of Aspect 15, wherein measuring a color dominant wavelength of each layer further comprises using a broadband light source and a spectrometer.

Aspect 22. The method of Aspect 21, wherein the broadband light source includes a minimum of all wavelengths in a visible range of approximately 400-700 nm.

Aspect 23. The method of Aspect 21, wherein measuring a color dominant wavelength of each layer further comprises carrying the broadband light source to the separated fluid components via at least one optical fiber.

Aspect 24. The method of Aspect 21, wherein the broadband light source and spectrometer are configured to be connected to an optical fiber bundle including at least one optical fiber which carries light from the broadband light source to the fluid in the centrifugal separation chamber and at least one optical fiber that carries light reflected by the fluid in the centrifugal separation chamber to the spectrometer.

Aspect 25. The method of Aspect 24, wherein the optical fiber bundle includes a plurality of optical fibers that carry light from the broadband light source and are arranged around the at least one optical fiber that carries reflected light to the spectrometer.

Aspect 26. The method of Aspect 24, wherein the optical fibers of the optical fiber bundle are placed at a selected acute angle relative to a surface of the centrifugal separation chamber containing the fluid being processed.

Aspect 27. The method of Aspect 26, wherein the selected acute angle is an angle between 30° and 60°.

Aspect 28. The method of Aspect 27, wherein the selected acute angle is 45°.

Aspect 29. A blood separation system, comprising: a centrifugal separator configured to receive a centrifugal blood separation chamber of a disposable fluid flow circuit and to process blood to separate at least one cellular component from plasma; a pump system configured to move the plasma in the disposable fluid flow circuit; an outlet associated with the blood separation chamber for removing at least a portion of the plasma from the blood separation chamber; a color-based interface monitoring system configured to directly monitor the interior of the blood separation chamber and to determine an interface position between the separated component and the plasma during a centrifugal separation procedure; and a controller configured to: control the pump system to convey a fluid into the centrifugal separation chamber; control the centrifugal separator to separate the blood in the centrifugal separation chamber into layers of plasma and the separated at least one cellular component with the interface located between the layers; measure a color of each layer via a dominant wavelength of reflected light; calculate a duration for each measured dominant wavelength associated with the respective layers; set a predetermined target color time as a setpoint for a selected layer; calculate an error signal; and utilize the error signal and calculate proportional-integral-derivative terms and a control signal that changes a pump system setting so as to adjust the interface position.

Aspect 30. The fluid separation device of Aspect 29, wherein the color-based interface monitoring system further comprises a broadband light source and a spectrometer.

Aspect 31. The fluid separation device of Aspect 30, wherein the broadband light source includes a minimum of all wavelengths in a visible range of approximately 400-700 nm.

Aspect 32. The fluid separation device of any of Aspects 30-31 wherein the broadband light source and spectrometer are configured in an optical fiber bundle including at least one optical fiber which carries light from the broadband light source to the plasma and the at least one cellular component in the centrifugal separation chamber and at least one optical fiber that carries light reflected by the plasma and the at least one cellular component in the centrifugal separation chamber to the spectrometer.

Aspect 33. The fluid separation device of Aspect 32, wherein the optical fiber bundle includes a plurality of optical fibers that carry light from the broadband light source and are arranged around the at least one optical fiber that carries reflected light to the spectrometer.

Aspect 34. The fluid separation device of any of Aspects 32-33, wherein the optical fibers of the optical fiber bundle are placed at a selected acute angle relative to a surface of the centrifugal separation chamber containing the blood being processed.

Aspect 35. The fluid separation device of Aspect 34, wherein the selected acute angle is an angle between 30° and 60°.

The invention claimed is:

1. A fluid separation device, comprising:

a centrifugal separator configured to receive a centrifugal separation chamber of a disposable fluid flow circuit, the centrifugal separation chamber having an annular channel and a ramp extending from a high-G side wall portion toward a low-G side wall portion across at least a portion of the annular channel of the centrifugal separation chamber;

a pump system configured to convey a fluid into the centrifugal separation chamber, and to remove a separated fluid component from the centrifugal separation chamber;

an outlet associated with the centrifugal separation chamber for removing at least a portion of the separated fluid component from the centrifugal separation chamber;

a color-based interface monitoring system configured to determine an interface position between separated fluid components continuously flowing through the centrifugal separation chamber based on color measurements of layers of the fluid during a centrifugal separation procedure;

wherein the color-based interface monitoring system further comprises a light source directed toward the ramp in the centrifugal separation chamber and a color measurement device which measures colors of dominant wavelengths of reflected light over time;

and a controller configured to:

control the pump system to convey a fluid into the centrifugal separation chamber;

control the centrifugal separator to separate the fluid in the centrifugal separation chamber into layers of separated fluid components with the interface position located between the layers of separated fluid components;

utilize the light source and color measurement device to measure a color of each layer of the respective separated fluid components via a dominant wavelength of reflected light;

calculate as a color time a duration of time over which the reflected light is present for each measured dominant wavelength associated with the respective layers of separated fluid components;

set a predetermined target color time as a setpoint for each layer;

calculate an error signal; and utilize the error signal and calculate proportional-integral-derivative terms and a control signal that changes a pump system setting so as to adjust the interface position.

2. The fluid separation device of claim 1, wherein the light source further comprises a broadband light source.

3. The fluid separation device of claim 2, wherein the broadband light source includes a minimum of all wavelengths in a visible range of approximately 400-700 nm.

4. The fluid separation device of claim 2, wherein the broadband light source further comprises at least one optical fiber.

5. The fluid separation device of claim 2, wherein the color measurement device further comprises a spectrometer, and the broadband light source and spectrometer are configured to be connected to an optical fiber bundle including at least one optical fiber which carries light from the broadband light source to the fluid in the centrifugal separation chamber and at least one optical fiber that carries light reflected by the fluid in the centrifugal separation chamber to the spectrometer.

6. The fluid separation device of claim 5, wherein the optical fiber bundle includes a plurality of optical fibers that carry light from the broadband light source and are arranged around the at least one optical fiber that carries reflected light to the spectrometer.

7. The fluid separation device of claim 5, wherein the optical fibers of the optical fiber bundle are placed at a selected acute angle relative to a surface of the ramp in the centrifugal separation chamber containing the fluid being processed.

8. The fluid separation device of claim 7, wherein the selected acute angle is an angle between 30° and 60°.

9. The fluid separation device of claim 1, wherein the error signal for a selected layer is equal to the target color time minus the calculated color time for the selected layer.

10. The fluid separation device of claim 1, wherein the fluid comprises anticoagulated whole blood, the interface is between red blood cells and plasma, and the separated fluid component is the plasma.

11. The fluid separation device of claim 1, wherein the fluid separation device is configured to process blood to separate at least one cellular component from plasma.

12. The fluid separation device of claim 1, wherein the controller is further configured to repeatedly:

utilize the light source and color measurement device to measure a color of each layer of the respective separated fluid components via a dominant wavelength of reflected light;

calculate as a color time a duration of time over which the reflected light is present for each measured dominant wavelength associated with the respective layers of separated fluid components;

set a predetermined target color time as a setpoint for the interface position;

calculate an error signal; and utilize the error signal and calculate proportional-integral-derivative terms and a control signal that changes a pump system setting so as to adjust the interface position.

13. The fluid separation device of claim 1, wherein the fluid comprises anticoagulated whole blood, the interface is between red blood cells and platelet-rich plasma, the separated fluid component is the platelet-rich plasma, and the controller is further configured to repeatedly complete a routine of calculating the duration as the color time for the measured dominant wavelength of the platelet-rich plasma layer, calculating the error signal, utilizing the error signal to calculate proportional-integral-derivative terms and to calculate the control signal, and using the calculated control signal to change the pump system setting to adjust the interface position.

14. A blood separation system, comprising:

a centrifugal separator configured to receive a centrifugal blood separation chamber of a disposable fluid flow circuit, the centrifugal separation chamber having an annular channel and a ramp extending from a high-G side wall portion toward a low-G side wall portion across at least a portion of the annular channel of the centrifugal separation chamber and to process blood to separate at least one cellular component from plasma;

a pump system configured to move the plasma in the disposable fluid flow circuit;

an outlet associated with the blood separation chamber for removing at least a portion of the plasma from the blood separation chamber;

a color-based interface monitoring system configured to directly monitor the interior of the blood separation chamber and to determine an interface position between the separated component and the plasma during a centrifugal separation procedure;

wherein the color-based interface monitoring system further comprises a light source directed toward the ramp in the centrifugal separation chamber and a color measurement device which measures colors of dominant wavelengths of reflected light over time;

and a controller configured to:

control the pump system to convey a fluid into the centrifugal separation chamber;

control the centrifugal separator to separate the blood in the centrifugal separation chamber into layers of plasma and the separated at least one cellular component with the interface position located between the layers;

utilize the light source and color measurement device to measure a color of each layer via a dominant wavelength of reflected light;

calculate as a color time a duration of time over which the reflected light is present for each measured dominant wavelength associated with the respective layers;

set a predetermined target color time as a setpoint for a selected layer;

calculate an error signal equal to the target color time minus the calculated color time for the selected layer;

calculate proportional-integral-derivative terms and a control signal; and utilize the error signal and calculate proportional-integral-derivative terms and a control signal that changes a pump system setting so as to adjust the interface position.

15. The fluid separation device of claim 14, wherein the light source further comprises a broadband light source.

16. The fluid separation device of claim 15, wherein the broadband light source includes a minimum of all wavelengths in a visible range of approximately 400-700 nm.

17. The fluid separation device of claim 15, wherein the color measurement device further comprises a spectrometer, and the broadband light source and spectrometer are configured in an optical fiber bundle including at least one optical fiber which carries light from the broadband light source to the plasma and the at least one cellular component in the centrifugal separation chamber and at least one optical fiber that carries light reflected by the plasma and the at least one cellular component in the centrifugal separation chamber to the spectrometer.

* * * * *